United States Patent
Boyd et al.

(10) Patent No.: US 8,206,175 B2
(45) Date of Patent: Jun. 26, 2012

(54) VISUAL INDICATOR OF PROPER INTERCONNECTION FOR AN IMPLANTED MEDICAL DEVICE

(75) Inventors: Garth W. Boyd, Ellington, CT (US); Aaron Engel, Wethersfield, CT (US); Dana Dubuc, Tarpon Springs, FL (US); Edward F. Smith, III, Madison, CT (US); Michael E. Poppy, New Richmond, WI (US); Michael E. Grant, Cambridge, MN (US)

(73) Assignee: Deringer-Ney, Inc., Bloomfield, CT (US)

( * ) Notice: Subject to any disclaimer, the term of this patent is extended or adjusted under 35 U.S.C. 154(b) by 40 days.

(21) Appl. No.: 12/857,236

(22) Filed: Aug. 16, 2010

(65) Prior Publication Data
US 2011/0039445 A1 Feb. 17, 2011

Related U.S. Application Data

(63) Continuation-in-part of application No. 12/727,955, filed on Mar. 19, 2010, now Pat. No. 7,942,686, which is a continuation-in-part of application No. 12/061,246, filed on Apr. 2, 2008, now Pat. No. 7,690,953.

(60) Provisional application No. 60/915,765, filed on May 3, 2007, provisional application No. 61/242,460, filed on Sep. 15, 2009.

(51) Int. Cl.
*H01R 3/00* (2006.01)
(52) U.S. Cl. .................. 439/490; 439/717; 439/909
(58) Field of Classification Search .................. 439/490, 439/489, 717, 909
See application file for complete search history.

(56) References Cited

U.S. PATENT DOCUMENTS

| | | | |
|---|---|---|---|
| 3,001,170 A | 9/1961 | Eyre et al. | |
| 3,187,295 A | 6/1965 | Huska | |
| 3,215,973 A | 11/1965 | Falconer | |
| 3,848,951 A | 11/1974 | Michaels et al. | |

(Continued)

FOREIGN PATENT DOCUMENTS
EP 1 737 078 A1 12/2006
(Continued)

OTHER PUBLICATIONS http://www.integra-ls.com/products/?product=55 website, first published Aug. 16, 2004.
(Continued)

*Primary Examiner* — Hae Moon Hyeon
(74) *Attorney, Agent, or Firm* — Dorsey & Whitney LLP

(57) ABSTRACT

During implant of an implantable medical device, implanted cables or leads are inserted to a connector block. An insertion indicator provides the user with a visual indication the cables or leads have been correctly inserted into the connector block, which enables the implanted medical device to properly deliver treatment or receive signals via the implanted cables or leads. The insertion indicator may be provided by a mechanical indicator optically viewable once the lead has been correctly inserted, and/or may be provided by an electrically activated light indicator illuminated by a power source associated with the connector block or with a connector tool used to connect the lead or cable to the connector block upon correct insertion of the lead or cable. The insertion indicator may be permanently or removably disposed on the connector block, a connector tool, and/or a can associated with the connector block.

20 Claims, 37 Drawing Sheets

U.S. PATENT DOCUMENTS

| | | | |
|---|---|---|---|
| 4,070,086 A | | 1/1978 | Trafford |
| 4,077,697 A | | 3/1978 | Yates |
| 4,401,958 A | | 8/1983 | Noorigian |
| 4,537,457 A | | 8/1985 | Davis, Jr. et al. |
| 5,022,404 A | | 6/1991 | Hafner |
| 5,222,164 A | * | 6/1993 | Bass, Sr. et al. ............. 385/14 |
| 5,380,214 A | * | 1/1995 | Ortega, Jr. .................. 439/253 |
| 5,645,577 A | | 7/1997 | Froberg et al. |
| 5,690,509 A | * | 11/1997 | Eisenbraun .................. 439/490 |
| 5,704,802 A | * | 1/1998 | Loudermilk ................. 439/490 |
| 5,755,743 A | | 5/1998 | Volz et al. |
| 5,843,141 A | | 12/1998 | Bischoff et al. |
| 5,951,595 A | | 9/1999 | Moberg et al. |
| 6,016,447 A | | 1/2000 | Juran et al. |
| 6,016,448 A | | 1/2000 | Busacker et al. |
| 6,029,089 A | | 2/2000 | Hawkins et al. |
| 6,080,188 A | | 6/2000 | Rowley et al. |
| 6,112,121 A | | 8/2000 | Paul et al. |
| 6,154,675 A | | 11/2000 | Juran et al. |
| 6,293,596 B1 | | 9/2001 | Kinder |
| 6,312,297 B1 | | 11/2001 | Lorkowski |
| 6,321,126 B1 | | 11/2001 | Kuzma |
| 6,390,843 B1 | | 5/2002 | Lim |
| 6,409,530 B1 | * | 6/2002 | Zhao et al. .................. 439/188 |
| 6,428,368 B1 | | 8/2002 | Hawkins et al. |
| 6,551,142 B2 | * | 4/2003 | Eisenbraun .................. 439/668 |
| 6,721,600 B2 | | 4/2004 | Jorgenson et al. |
| 6,878,013 B1 | | 4/2005 | Behan |
| 6,929,517 B2 | | 8/2005 | Tsai |
| 6,963,780 B2 | | 11/2005 | Ruben et al. |
| 6,971,907 B1 | * | 12/2005 | Stroud ......................... 439/490 |
| 7,012,542 B2 | | 3/2006 | Powell et al. |
| 7,047,083 B2 | | 5/2006 | Gunderson et al. |
| 7,070,455 B2 | | 7/2006 | Balsells |
| 7,087,077 B1 | | 8/2006 | Van Dijk et al. |
| 7,128,757 B2 | | 10/2006 | Boylan et al. |
| 7,187,975 B2 | | 3/2007 | Flickinger et al. |
| 7,195,523 B2 | | 3/2007 | Naviaux |
| 7,244,150 B1 | | 7/2007 | Brase et al. |
| 7,286,882 B2 | | 10/2007 | Cole |
| 7,347,751 B2 | | 3/2008 | Sweeney et al. |
| 7,510,447 B2 | | 3/2009 | Drew |
| 7,526,339 B2 | | 4/2009 | Lahti et al. |
| 7,534,127 B2 | | 5/2009 | Parker et al. |
| 7,798,864 B2 | | 9/2010 | Barker et al. |
| 7,819,682 B2 | | 10/2010 | Donetsky |
| 2001/0053631 A1 | | 12/2001 | Nagai |
| 2002/0002016 A1 | | 1/2002 | Sato et al. |
| 2004/0106964 A1 | | 6/2004 | Fischer, Sr. et al. |
| 2004/0153138 A1 | | 8/2004 | Murphy |
| 2004/0162593 A1 | | 8/2004 | Jorgenson et al. |
| 2005/0186829 A1 | | 8/2005 | Balsells |
| 2007/0161294 A1 | | 7/2007 | Brase et al. |
| 2007/0179553 A1 | | 8/2007 | Iyer et al. |
| 2007/0225772 A1 | | 9/2007 | Lahti et al. |
| 2007/0280850 A1 | | 12/2007 | Carlson |
| 2008/0195194 A1 | | 8/2008 | Pacetti et al. |
| 2008/0274651 A1 | | 11/2008 | Boyd et al. |
| 2011/0022100 A1 | | 1/2011 | Brase et al. |
| 2011/0151698 A1 | * | 6/2011 | Boyd et al. .................... 439/246 |

FOREIGN PATENT DOCUMENTS

| | | |
|---|---|---|
| GB | 2227612 | 8/1990 |
| WO | WO 02/095877 A1 | 11/2002 |
| WO | WO 2007/070544 | 6/2007 |

OTHER PUBLICATIONS

Harris et al., "A study of some palladium-tin, silver-tin and palladium-silver-tin alloys," *Journal of the Less-Common Metals*, Elsevier-Sequoia, S.A. Lausanne, CH, 16(3): 223-232 (Nov. 1, 1968).

Schenck, J.F., "The Role of Magnetic Susceptibility in Magnetic Resonance Imaging: MRI Magnetic Compatibility of the First and Second Kinds," Medical Physics, AIP, Melville, NY, vol. 23, No. 6 (Jun. 1, 1996).

* cited by examiner

FIG 11B
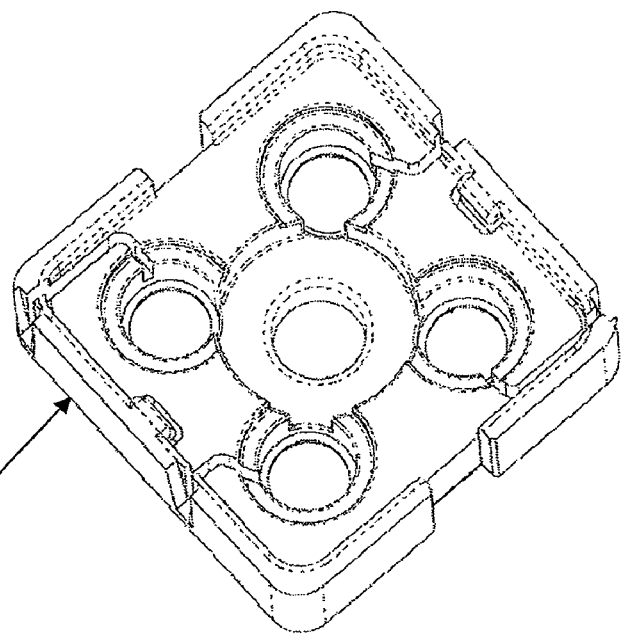
102
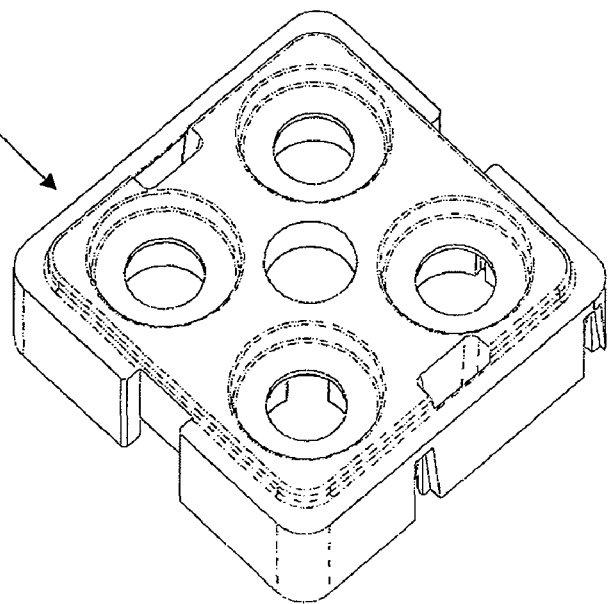
FIG 11C

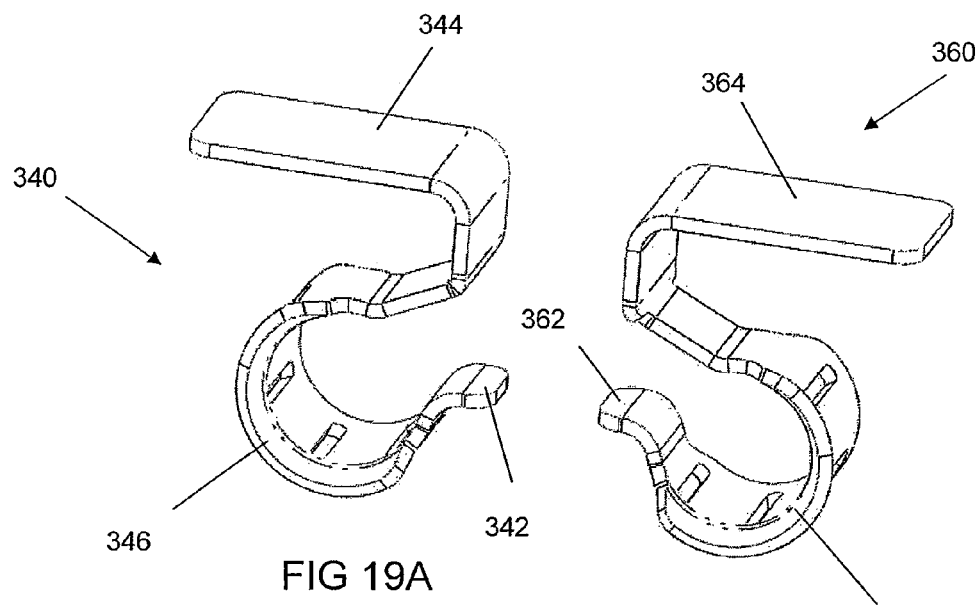
FIG 19A
FIG 19B
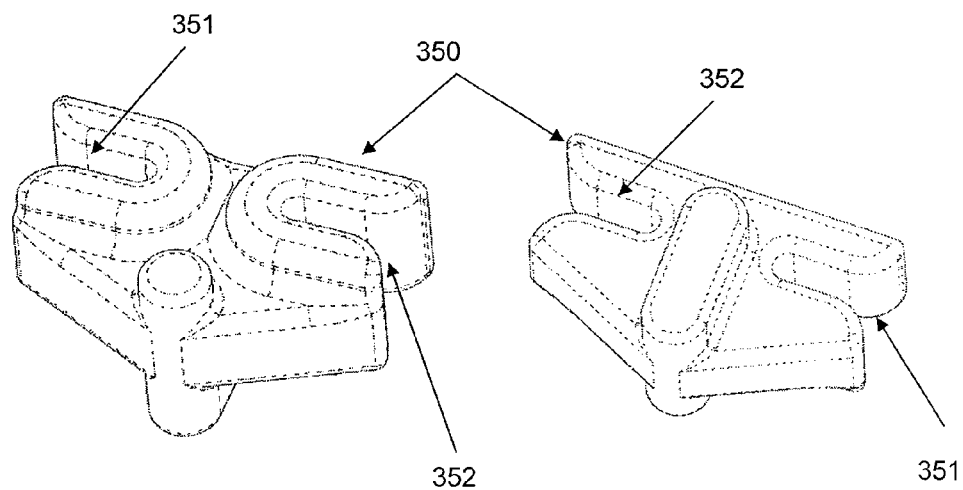
FIG 20A
FIG 20B

VISUAL INDICATOR OF PROPER INTERCONNECTION FOR AN IMPLANTED MEDICAL DEVICE

CROSS REFERENCE TO RELATED APPLICATION

This application is a continuation-in-part ("CIP") application of U.S. application Ser. No. 12/727,955, filed Mar. 19, 2010, which is a CIP of U.S. application Ser. No. 12/061,246, filed Apr. 2, 2008, entitled "A Stackable Electrical Connection Apparatus", now U.S. Pat. No. 7,690,953, which claims benefit under 35 U.S.C. §119(e) to U.S. Ser. No. 60/915,765, entitled "Electrical Connection Apparatus", filed May 3, 2007, and this application claims priority to U.S. Application No. 61/242,460, entitled "Electrical Barrier and Moisture Seal for an Implanted Medical Device," filed Sep. 15, 2009. The content of each application is incorporated herein by reference in its entirety.

FIELD OF THE INVENTION

Disclosed herein are apparatuses for visually indicating to an operator the quality, correctness and/or optimization of the interconnection of major components of an implanted medical device. In particular, the apparatuses indicate the alignment status of implanted leads or catheters in connection with an implanted control device.

BACKGROUND

Active medical devices for delivering stimulation therapy to body organs such as the heart, brain, or other tissues are typically comprised of two major components. One component is an electronic circuit and power source, typically a battery, housed in a hermetically sealed container, often referred to as the implantable pulse generator (IPG), or as the "can". The container includes feed-throughs allowing electrical signals and power to pass through the hermetic containment in and out of the circuitry to the second major component, the lead. This lead carries electrical signals from the IPG to the target body tissue in order to deliver therapy. The lead may also house conductors that carry signals generated by the human body back to the IPG.

The conductors within the lead are exposed at electrode sites on the distal end of the lead and interface by direct contact with body tissues. At the proximal end of the lead, the conductors are again exposed. Various forms of metallic rings, or segments, or end protruding pins are used to make the conductors available at the outer surface of the lead. The proximal end of the lead is inserted into the receptacle of the IPG and the lead's conductors are aligned with mating conductive surfaces inside the receptacle.

For the interconnection of the lead and the IPG it is essential that the exposed conductive surfaces on the lead to align with the conductive surfaces in the receptacle of the IPG. This alignment is accomplished at the time the medical device system is implanted by the implanting medical personnel. There may be one or a plurality of leads to be inserted and correctly aligned, and the environment in the surgical arena makes it difficult for the implanting medical personnel to be sure each lead is fully and functionally inserted, before leaving the medical device in the patient's body and closing the surgical wound.

SUMMARY

Accordingly, an objective of this invention is to provide a visual indication to the implanting medical personnel that shows when a lead is in an optimal, aligned and/or correct position in which the lead is aligned with and/or in electrical contact with electrical connection contacts associated with the electrical connection apparatus.

One embodiment of such an indicator may be provided by a mechanical and optical indicator. This example of an indicator may include an encapsulation material that is transparent to visible light and covers or protects the connector and any indicators. As the lead is inserted into the IPG's receptacle and pushed deeper into the receptacle, the proximal end of the lead touches a small moveable element at the disposed within the receptacle. Continuing to force the lead further into the receptacle urges the moveable element forward as well. This moveable element provided by the indicator would have a clear indication in the form of a line, or a color change, or other fiducial mark that would be illuminated by the ambient light in the room. Reflection from the moveable element would allow the fiducial mark to be visible to the user and indicate when the lead has been properly inserted. The moveable element may incorporate a mechanical energy storage component, such as a spring, to return the indicator to no longer show the fiducial mark, if the lead was subsequently withdrawn or misaligned during the implant procedure.

Another embodiment of an indicating system that demonstrates the implanted lead and the interior portions of the connector apparatus are correctly aligned includes a light indicator electrically illuminated upon reaching each lead's full insertion point. Indicator lights may be positioned on the surface of the connector block or recessed therein. The lights would be visible through a transparent encapsulation or overmolded material at the connector block surface. A method of energizing such an illuminated annunciator may involve providing electrical conductors extending from at least two points on the surface of the connector apparatus, which would conduct electricity from an outside power source (e.g., a power source external to the connector block) to a light source incorporated into the exterior body surface of the connector block or at least one stackable block along with a switch. The switch would normally be open, and would be urged to a closed condition by the force imposed by the advancing lead as the lead enters the connector apparatus. The switch would be positioned so as to be closed when the lead was in proper position, so that an electrical circuit is completed, thus causing the light source to emit light, indicating the satisfactory alignment.

According to certain embodiments, the indicator is an LED light source with associated electrical conductors originating at the point where the operating tool engages the connector apparatus. A battery in the operating tool or wrench is provided as an external power source and supplies electrical current to a small switch to illuminate the LED indicator located at the end of the connector apparatus. One or multiple LED indicators may be provided, for example, depending on the number of leads associated with one connector apparatus.

In another embodiment, the indicator is an indicator switch and an electrical conductor is provided within the connector apparatus at the point where the operating tool engages the connector apparatus. A battery in the operating tool or wrench supplies electrical current to the indicator switch provided at an end of the connector apparatus. One or multiple switches may be provided, for example, depending on whether multiple leads are associated with one connector apparatus. Switches may also be associated with the connector apparatus that are supplied with electrical current when the external power source is coupled (i.e., to confirm the coupling between the connector apparatus and the power source) and when mechanics of the connector apparatus have moved or changed state. Each switch in the connector apparatus associates with a resistance element unique to the corresponding switch, and differing resistance values provide a unique identification for each permutation of switch closures. The operating tool incorporates electrical circuits that discriminate the pattern of switch closures and illuminate indicators on the surface of the tool, thus showing the status of the one or more leads' position. The indicators may illuminate only when correct position is achieved, or several indicators may be provided for indicating both proper position and for misalignment. For example, a green LED may be used for optimal position of the lead, power source or connector components, and a red LED may be used to indicate non-optimal positioning. In another example, a red LED may be illuminated prior to lead insertion and where the lead is misaligned, and may subsequently be turned off when the proper lead position has been achieved.

The connector apparatus may include switches that would be in the open state when the apparatus is in the open or un-latched condition. Rotation of the latching shaft to the latched position closes the switch, and incorporates an additional resistive element used by the electronics of the tool to discriminate the latched and un-latched states. An additional indicator or indicators on the surface of the tool would show this connector status in addition to the position status of the one or multiple leads.

While multiple embodiments of the present invention are disclosed herein, still other embodiments of the present invention will become apparent to those skilled in the art from the following detailed description, which shows and describes illustrative embodiments of the invention. As will be realized, by those of ordinary skill in the art upon reading the following disclosure, the invention is capable of modifications in various aspects, all without departing from the spirit and scope of the present invention. Accordingly, the drawings and detailed description are to be regarded as illustrative in nature and not restrictive.

BRIEF DESCRIPTION OF THE FIGURES

FIGS. 11A-C depict a block of the apparatus depicted in FIG. 10.

FIGS. 19A-B depict perspective views of electrical connection contacts for use on a left and a right side of the stackable block.

FIGS. 20A-B depict perspective views of a first and second side of a slider for use with the stackable block.

DETAILED DESCRIPTION

The present invention, according to one embodiment, is an electrical connection apparatus.

In one aspect, an electrical connection apparatus may be used in conjunction with implantable medical devices such as neurostimulators or pacemakers. For example, such an apparatus may be used to provide an electrical connection between the implanted device and an implanted stimulation electrode. In one embodiment, the implanted device is a pacemaker. Alternatively, the implanted device may be an implantable cardioverter defibrillator ("ICD"), an implantable pulse generator, or any other implanted device requiring an electrical connection.

Figure 1:
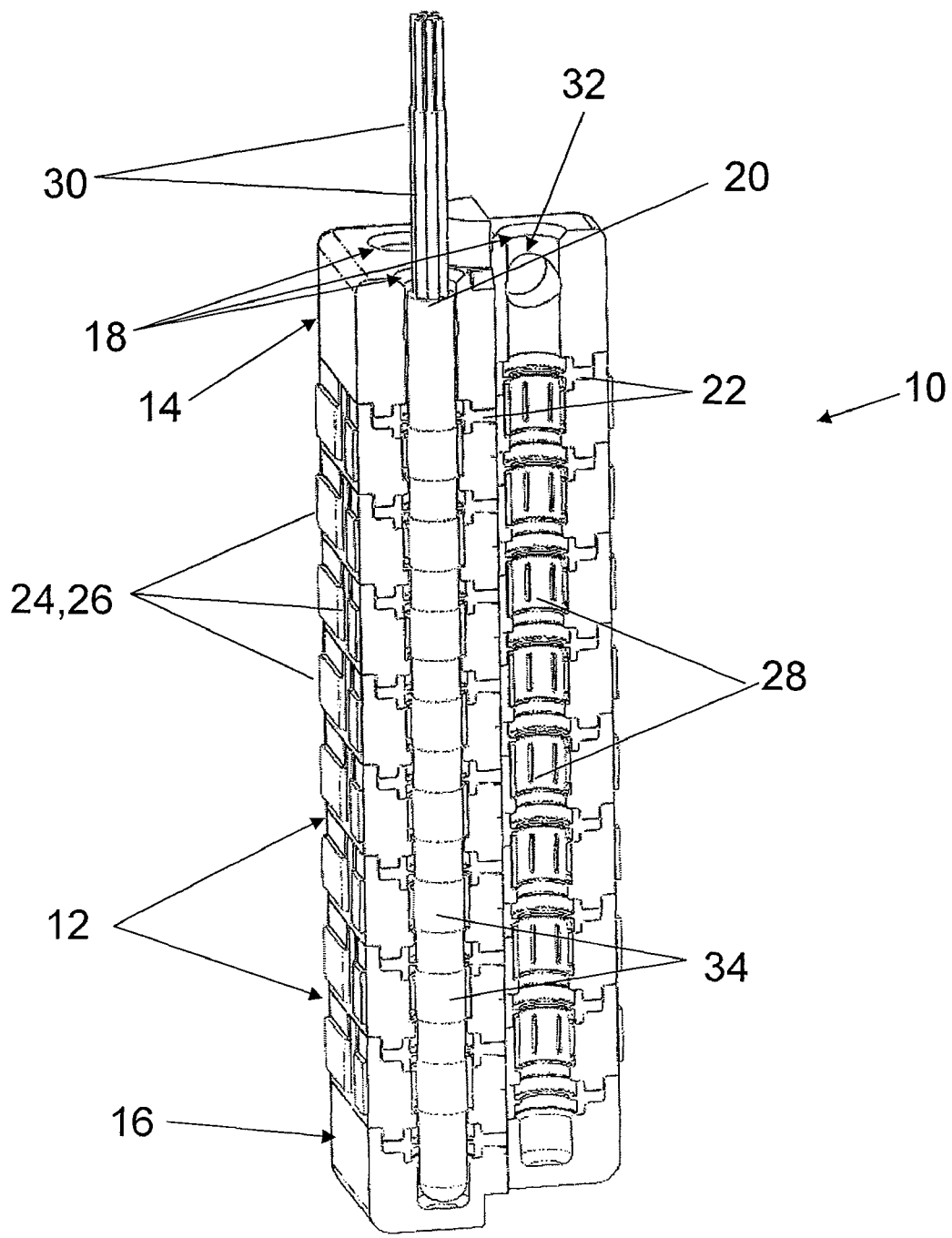
FIG. 1 is cutaway view of one embodiment of an electrical connection apparatus.

FIG. 1 is a cutaway view of one embodiment of an electrical connection apparatus 10. The apparatus is comprised of stackable blocks 12 operably connected in a stacked fashion, with end blocks 14, 16 disposed at each end. Each block 12, 14, 16 defines pin receiving portions 18 configured to receive a pin such as pin 20 depicted in FIG. 1. In addition, a seal component 22 is disposed between each block 12, 14, 16. Each block 12, in this implementation, also has electrical connection contacts 24 having exterior contact points 26 (also referred to herein as "leads") disposed on an exterior portion of the device 10 and integrally formed C-shaped interior contact portions 28 disposed within the pin receiving portions 18.

Generally, the connection apparatus 10 depicted in FIG. 1 connects two devices or components in the following fashion. The pin 20, which is electrically coupled to one device via the lead wires 30, is positioned in one of the pin receiving portions 18 and thereby contacts one or more of the interior contact portions 28 of the electrical connection contacts 24. The other device is positioned or configured such that it is in electrical contact with one more of the exterior contact portions 26 of the electrical connection contacts 24. Thus, the two devices are electrically coupled to each other via the electrical connections contacts 24 disposed within each block 12 of the apparatus 10.

In the embodiment depicted in FIG. 1, the apparatus 10 has eight connector blocks 12. However, it is understood that the apparatus 10 may be comprised of one block 12, two blocks 12, or any number of blocks 12 in order to provide a connection device 10 with the desired size and configuration. End blocks 14, 16 may be used as the end termination for each end of the electrical apparatus 10. End block 14 is also referred to herein as an "insertion end block," while end block 16 is also referred to herein as an "end cap block." The blocks 14, 16 may be manufactured out of metals such as titanium, stainless steel or other biocompatible metals or metallic alloys. Alternatively, the blocks 12, 14, 16 may be made of biocompatible thermoset or thermoplastic resins, or any other known biocompatible material for use in connection devices According to the implementation depicted in FIG. 1, the insertion end block 14 defines mechanical fastening ports 32 for each of the pins 20. Each port 32 may be configured to be in communication with one of the pin receiving portions 18 such that each port 32 may receive a fastening component (not shown) that may be used to fasten or otherwise secure the pin 20 into its position in that pin receiving portion 18. In one embodiment, the fastening component is a threaded set screw made from biocompatible material and each port 32 is a threaded hole configured to receive such a set screw. Alternatively, any known fastening component may be incorporated into the insertion end block 14. In one implementation, a cap or other type of cover may be provided and positioned over the fastening port 32, thereby presenting a relatively smooth external profile for the device 10. In a further alternative, the insertion end block 14 has no fastening ports or fastening components, and the pin 20 is at least partially secured within the pin receiving portions via frictional forces created by contact with the C-shaped contact portions 28.

In use, and in accordance with one aspect, after the pin 20 is positioned in the pin receiving portion 18, the set screw is threaded into the port 32 such that the set screw contacts the pin 20 at an electrically isolated portion of pin 20, and secures pin 20 in the pin receiving portions 18. It acts to supplement the frictional forces exerted by the C-shaped contact portions 28 and helps prevent outward migration of the pin from the housing caused by vibration or excessive tensile or torsional forces on the pin 20 or lead wires 30 during use.

In one implementation as shown in FIG. 1, pin 20 has electrically-isolated circumferential contacts 34 distributed along its length. When the pin 20 is positioned in a pin receiving portion 18, each of the circumferential contacts 34 are positioned to correspond with and contact a C-shaped contact portion 28. Each circumferential contact 34 is electrically connected to one of the lead wires 30, each of which is embedded in the pin 20. Each individual wire or lead 30 may be potted within the pin 20 and may be electrically isolated and insulated from other leads. The pin 20 may contain one or more separate isolated lead wires 30 for each contact 34. Each wire 30 may be capable of maintaining signal integrity from the circumferential contact area 34 through the wire 30 and to a desired location within the body, such as a target tissue, nerve, or some other target area. In one embodiment, a wire 30 terminates with a specialized electrode (not shown) to improve signal delivery to the desired location.

Figure 2A:
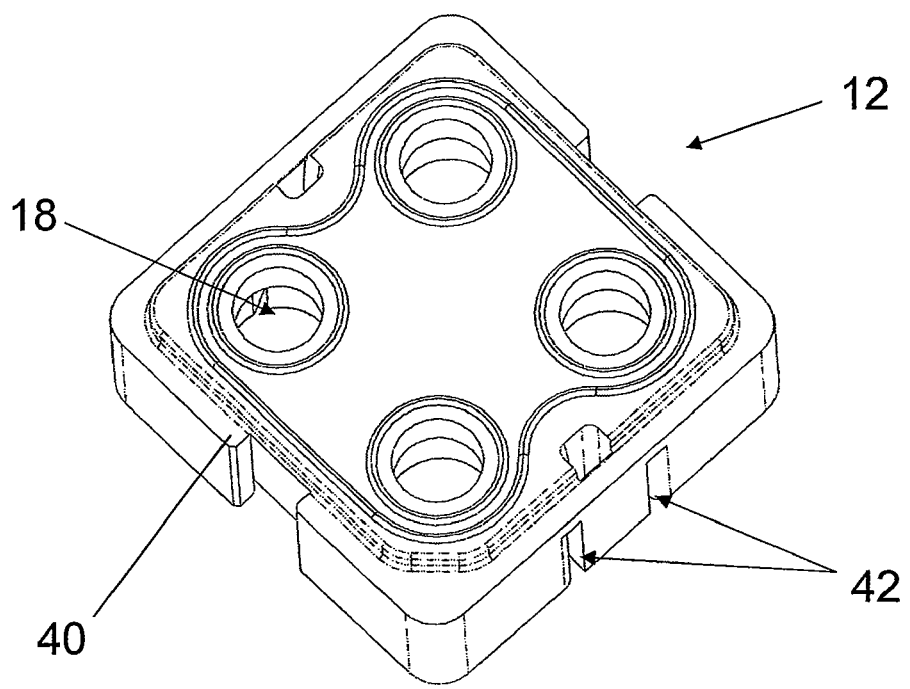
FIGS. 2A-B depict a first side and a second side of a connector block.
Figure 2B:
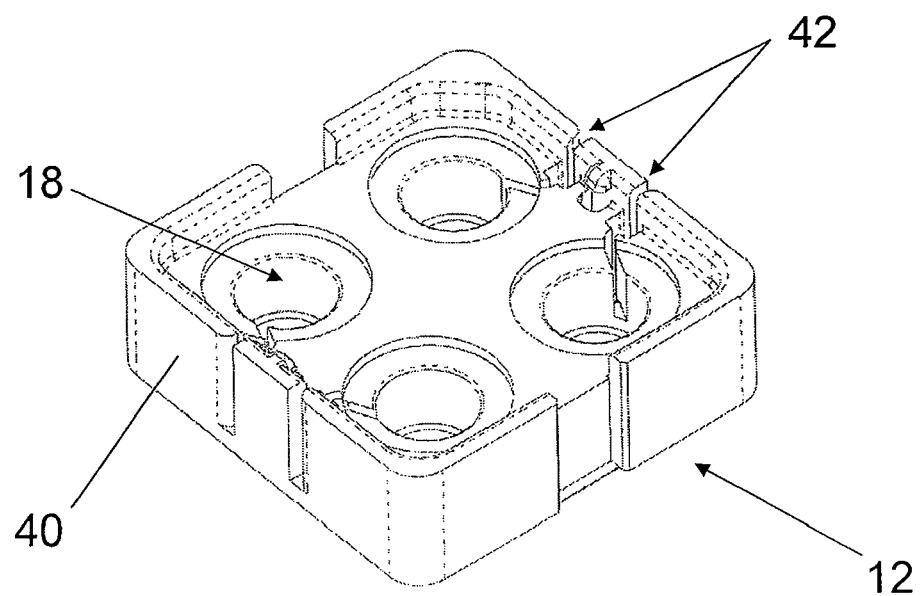
Figure 3A:
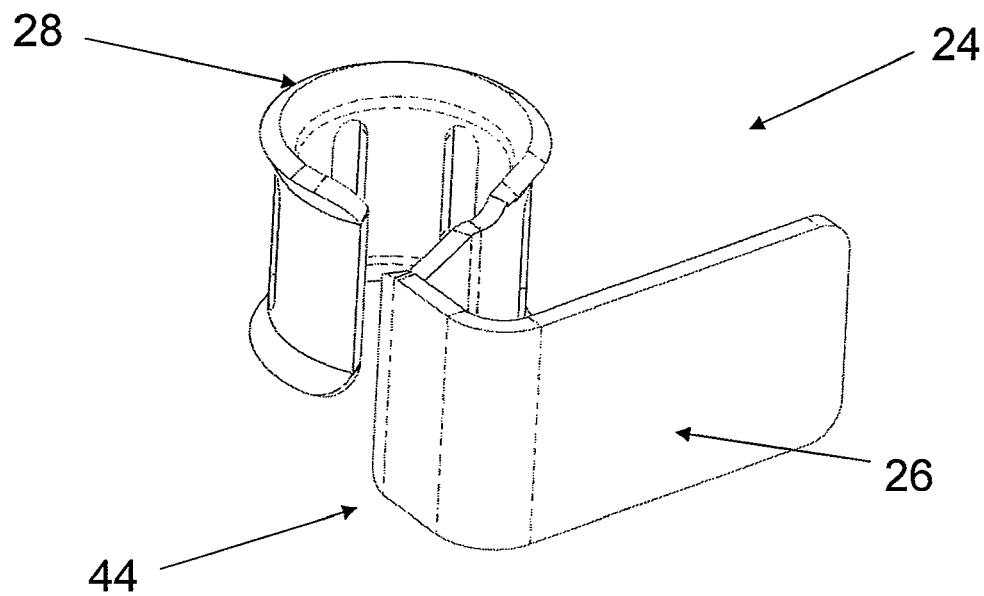
FIGS. 3A-B depict electrical connection contacts according to certain implementations.
Figure 3B:
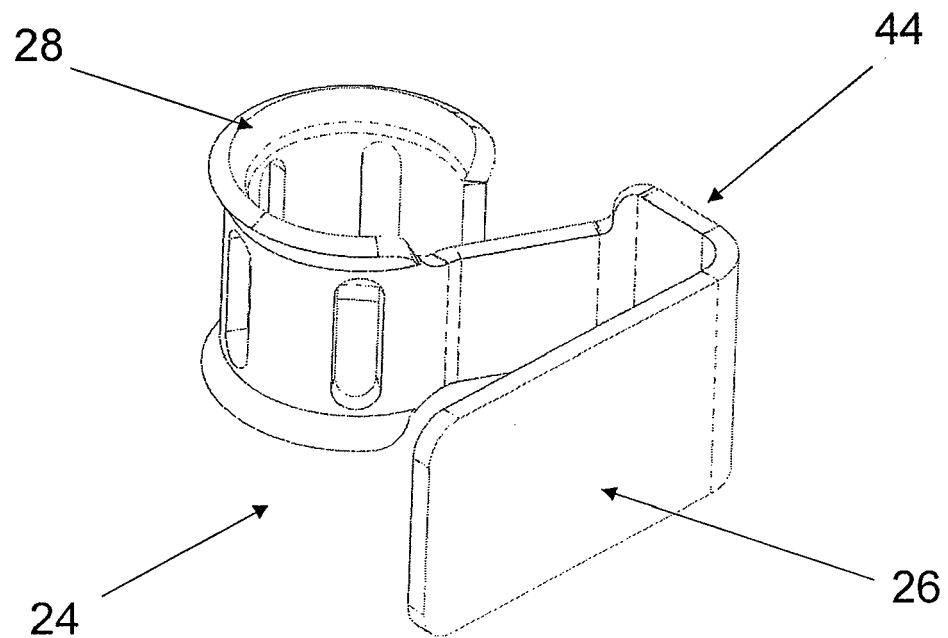

The configuration of a connector block 12 with electrical connection contacts 24, according to one embodiment, is shown in FIGS. 2A, 2B, 3, 4A, and 4B. FIGS. 2A and 2B depict both sides of a connector block 12 without electrical connection contacts, with FIG. 2A depicting a first side and FIG. 2B depicting a second side. The block 12 has a housing 40 that defines the pin receiving portions 18 and further defines slots or passages 42 in which portions of the electrical connection contacts may be disposed.

FIG. 3 depicts an electrical connection contact 24, in accordance with one implementation. The electrical connection contact 24 in this embodiment has a C-shaped contact portion 28 and an external lead portion 26. The contact portion 28 and lead portion 26 are connected via the link portion 44. In one embodiment as shown in FIG. 3, the C-shaped contact portion 28 defines slots or gaps. Alternatively, the contact portion 28 is a continuous, solid component with no slots or gaps.

Figure 4A:
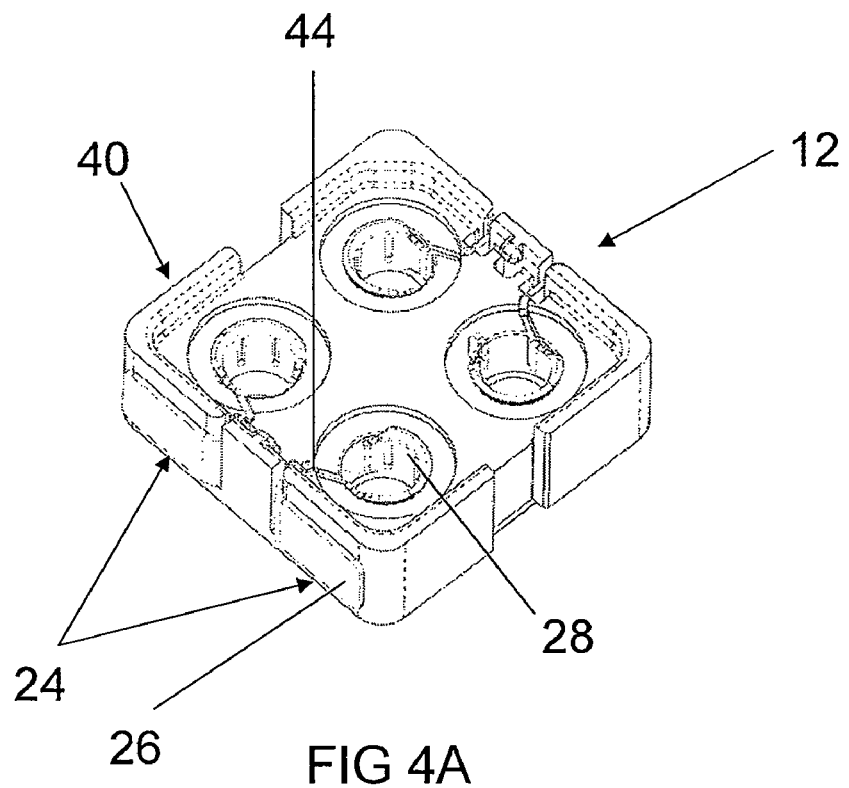
FIGS. 4A-B depict a first and second side of a connector block with four electrical connection contacts according to certain implementations.
Figure 4B:
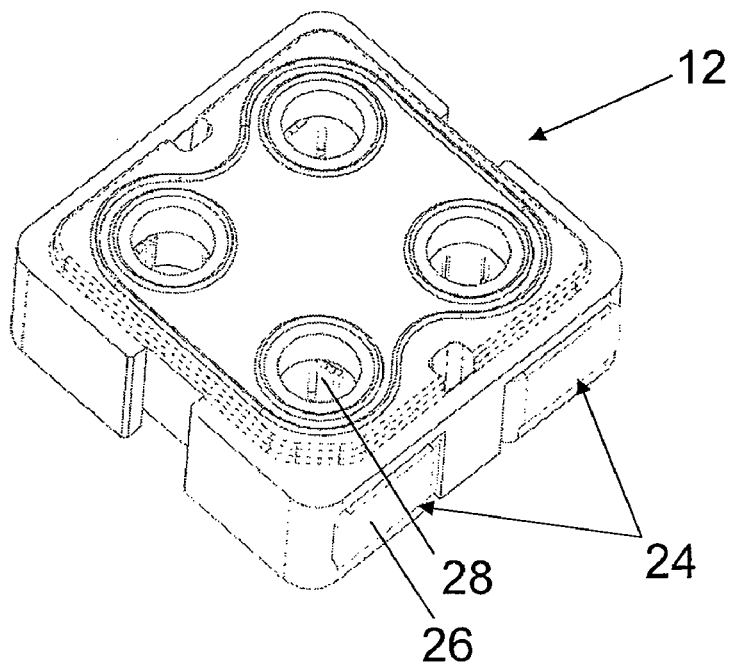
Figure 5E:
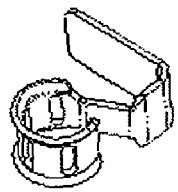
FIGS. 5A-5F depict additional embodiments of electrical connection contacts.
Figure 5D:
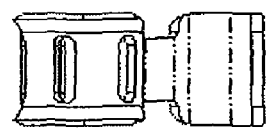
Figure 5F:
Figure 5B:
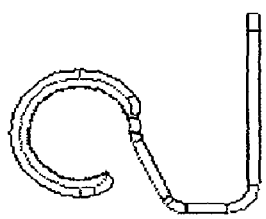
Figure 5C:
Figure 5A:
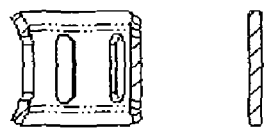

FIGS. 4A and 4B depict a first and second of connector block 12 with four electrical connection contacts 24, according to certain embodiments. Each electrical connection contact 24 may be positioned such that the C-shaped interior contact portion 28 is disposed within a pin receiving portion 18, the exterior contact portion 26 may be disposed on an exterior portion of the housing 40, and the link portion 44 may be disposed in one of the slots 42 as discussed above with respect to FIGS. 2A and 2B.

Each of the contact portions 28, according to one embodiment, is configured to contact any pin positioned in the pin receiving portion 18. In one embodiment, each contact portion 28 contacts a corresponding pin contact area 34 on the pin 20. Such contact results in an electrical connection between the lead 30 and the exterior contact points 26, via the electrical path from the lead 30 to the pin contact area 34 to the contact portion 28 to the link portion 44 to the exterior contact portion 26.

In accordance with one implementation, each C-shaped contact portion 28 is configured to have elastic properties and to have an unconstrained diameter (also referred to as its "unconstrained position," "natural position," "starting position," or "original position") that is smaller than the outside diameter ("OD") of the pin 20. "Elastic properties" as used herein means capable of recovering shape after deformation. Thus, when a pin 20 is positioned in the pin receiving portion 18, the contact portion 28 is deformed from its unconstrained diameter to a larger diameter that accommodates the pin 20. The elasticity of the contact portion 28 urges it back toward its unconstrained diameter such that the contact portion 28 is forced into contact with the pin 20 and results in a normal force being exerted across the contact interface. According to one embodiment, the contact portion 28 is forced into contact with a circumferential contact portion 34 on the pin 20. When the pin 20 is removed, the elastic properties of the contact portion 28 cause the contact portion 28 to return to its unconstrained diameter.

In another embodiment, the C-shaped contact portion 28 also has a maximum diameter that is limited by the diameter of the pin receiving portion 18. That is, the contact portion 28 may only expand to its maximum diameter, at which diameter the contact portion 28 is in contact with the walls of the pin receiving portion 18 and cannot expand further.

FIGS. 5A-5F depict additional embodiments of electrical connection contacts.

According to one embodiment, the electrical connection contacts are made out of a precious metal. For example, the contacts may be constructed of a platinum or PGM (Platinum Group Metal) alloy such as, but not limited to, Pt-10% Ir, Pt-20% Ir, Pt-8% W, Paliney® 500, Paliney® 1100, or Paliney® 1200. Alternatively, the contacts may be formed out of a base metal such as a copper alloy or stainless steel that is overplated with an appropriate electrically and environmentally stable contact material such as Au, Pt, Pd, Pd—Ni, etc. It is also envisioned that the overplate might cover the entire connection 24 or just the terminal contacts 26, 28. According to one embodiment, one advantage of precious metal contact surfaces in comparison to other conductive materials is that the precious metal contact surfaces are capable of maintaining stable electrical signal integrity at reduced force levels. This results in reduced force requirements at the mating of the contact portion 28 and the pin 20, thereby allowing for greater design flexibility in selecting the spring characteristics of the contact member 28. Alternatively, the electrical connection contacts may be made out of a non-PGM metal such as stainless steel, niobium, tantalum, MP35N, or other such non-PGM metals. Certain of these non-PGM metals may require higher contact forces to maintain a stable interface, which may be accomplished by selecting a material with a higher elastic modulus and/or a higher yield stress or by increasing the thickness of the spring member.

The seal component 22, as depicted in FIG. 1 according to one embodiment, is configured to be disposed between any two blocks (including the end blocks) and operates to create two seals. The first seal is a seal between the pin 20 and the rest of the block 12. The second seal is a seal between two connected blocks 12 and associated pin contact areas 34.

Figure 6:
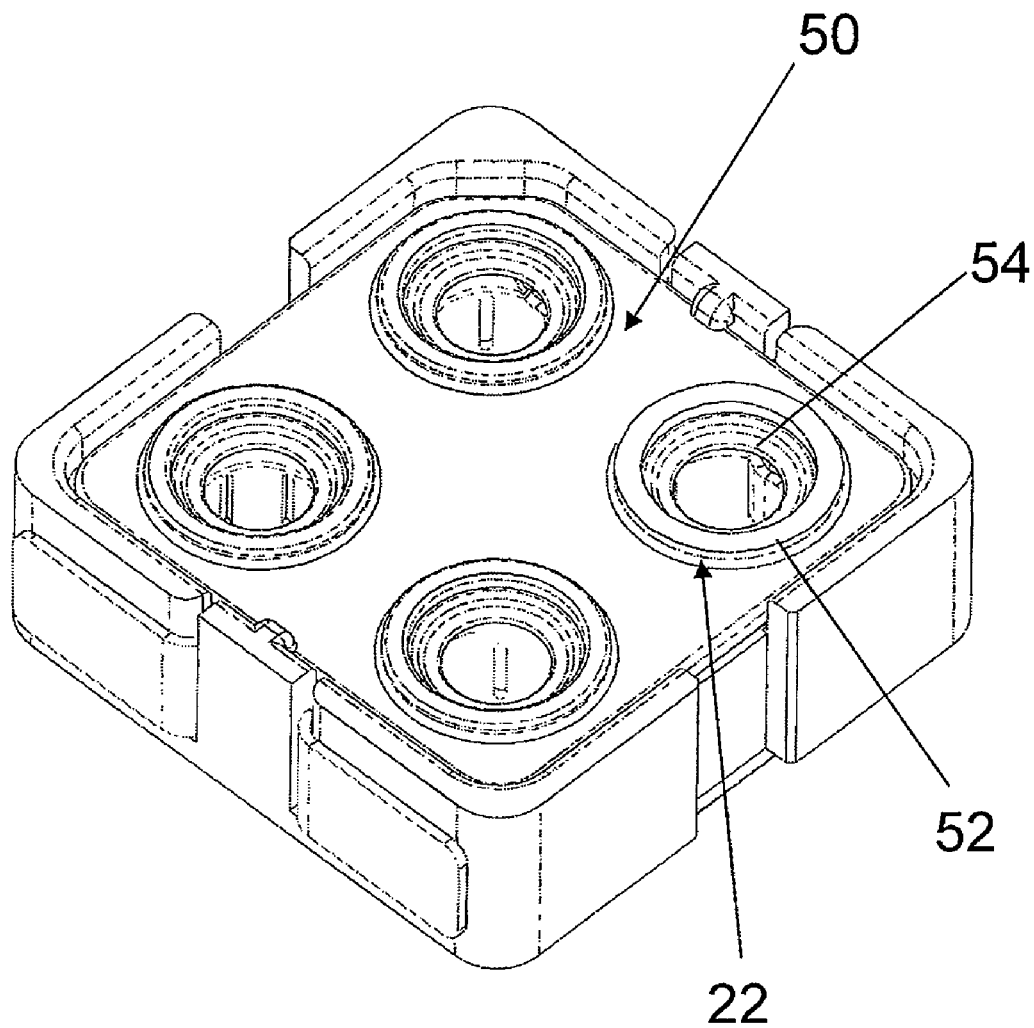
FIG. 6 depicts a seal component according to certain implementations.
Figure 7:
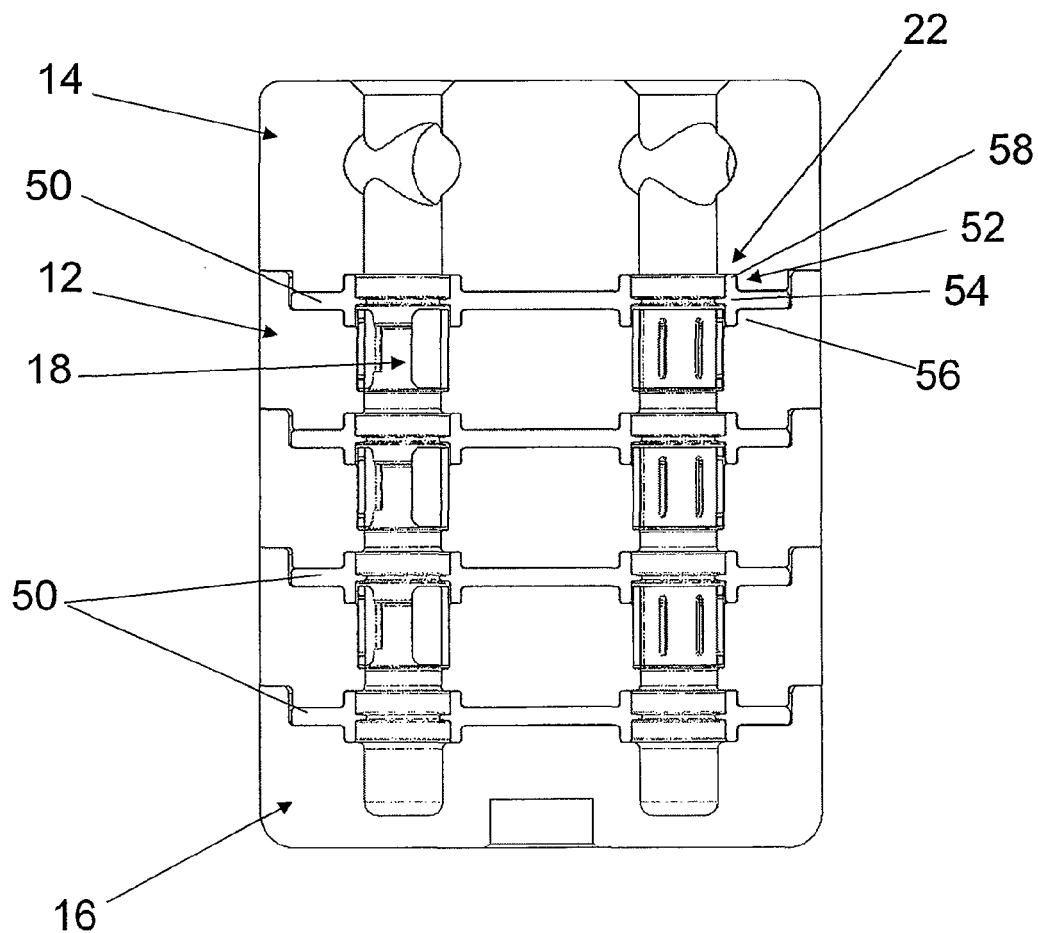
FIG. 7 depicts a seal component according to another implementation.

FIGS. 6 and 7 depict a seal component 22, according to another embodiment. In the embodiment depicted in FIG. 6, a seal plate 50 having four seal components 22 is positioned on one side of a connector block 12. Each seal component 22 disposed in the plate 50 has a "vertical" seal 52 and a "horizontal" seal 54 that completely encircle the pin 20 receiving portion 18 of the block 12. The terms "vertical" and "horizontal" are used solely to describe the seals with respect to each other and the connector blocks and are not intended to be limiting. It is understood that the vertical seal 52 could also be positioned horizontally and that the horizontal seal 54 could also be positioned vertically, depending on the disposition of the entire block. The combination of seals 52 and 54 result in a t-shaped seal component.

As best shown in FIG. 7, the vertical seal 52 of seal component 22 arranged in seal plate 50 provides a seal between the pin receiving portion 18 and the areas exterior to the pin receiving portion 18. In one embodiment, one end 56 of the vertical seal 52 contacts the block 12 next to which the plate 50 has been positioned and the other end 58 of the seal 52 contacts the adjacent block 14. According to one embodiment, the vertical seal 52 may form a seal that prevents body fluids from entering into the pin receiving portion 18, which may cause a short. In accordance with one implementation, the horizontal seal 54 of seal component 22 contacts any pin positioned in the pin receiving portion 18 and thereby provides a seal in the pin receiving portion 18 between blocks 12 and 14. As depicted by the positioning of seal plates 50 in FIG. 7, and in view of the discussion above, it should be understood that seal plate 50 may also be provided between adjacent stackable blocks 12 and between blocks 12 and 16.

Figure 8A:
FIGS. 8A-8D depict additional embodiments of seal components.
Figure 8B:
Figures 8C, 8D:
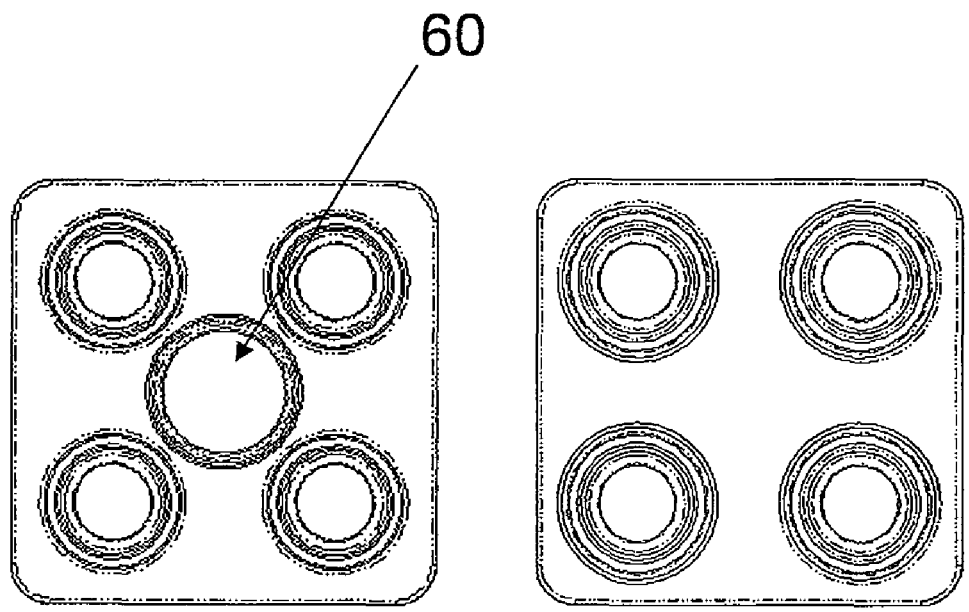

FIGS. 8A-8D depict additional embodiments of seal components. As shown in FIG. 8C, certain seal plates define a central opening 60. In certain embodiments, this central opening 60 may define a portion of a bolt shaft configured to receive a rotating cam or an assembly bolt, both of which are described below. Alternatively, certain seal plate embodiments such as that depicted in FIG. 8D have no central opening.

In one embodiment, a seal component is made out of biocompatible, compliant thermoset or thermoplastic polymer, such as, but not limited to, a silicone rubber. Alternatively, the seal component may be made of any known compliant biocompatible material that may be used for providing a seal in a medical device.

Figure 9:
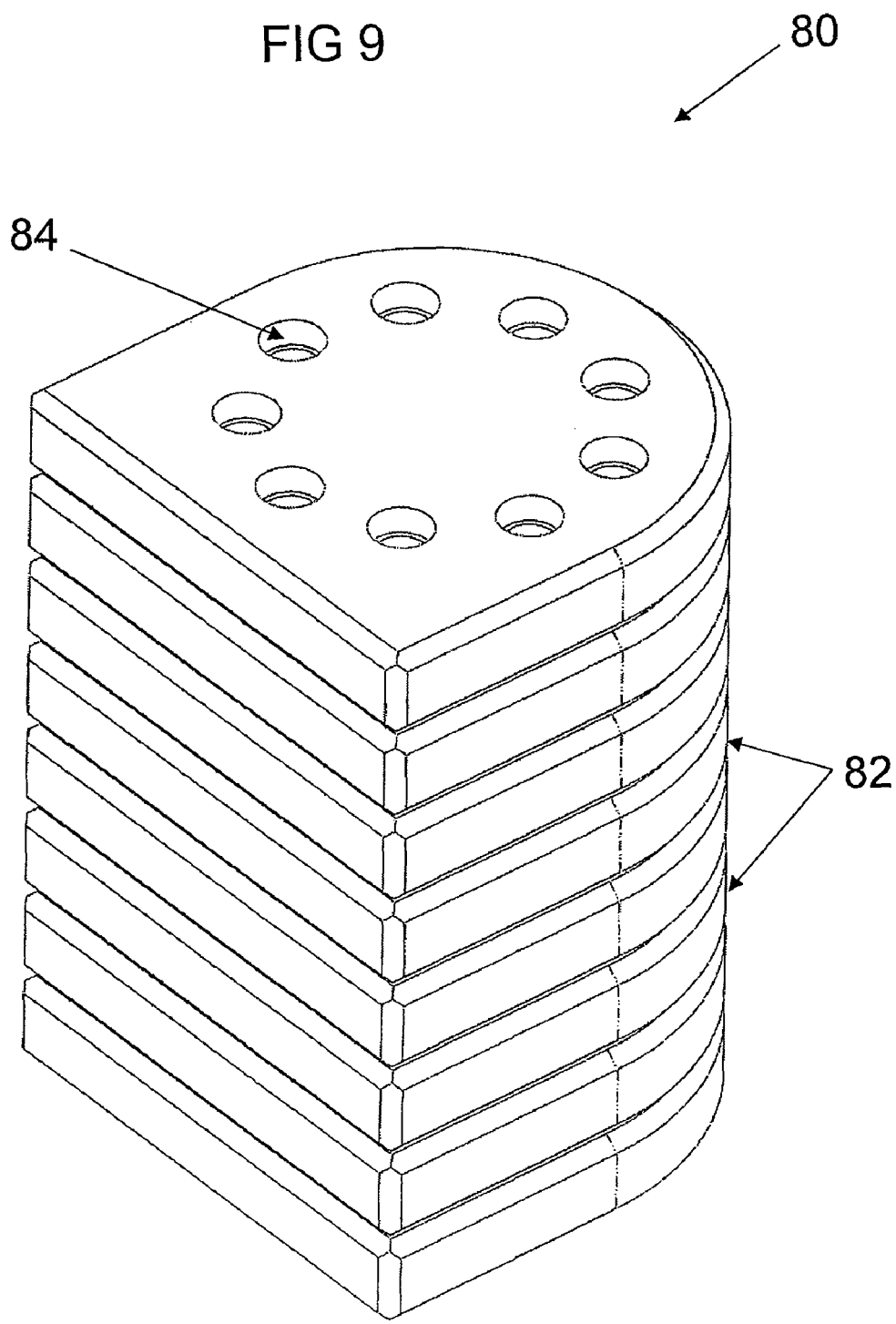
FIG. 9 depicts an alternative embodiment of an electrical connection apparatus having stackable connector blocks.

FIG. 9 depicts an alternative embodiment of a connector apparatus 80 having stackable connector blocks 82. In this embodiment, each block 82 has a D-shaped configuration and defines nine pin receiving portions 84. Alternatively, the block 82 may define any number of pin receiving portions that will fit on the block 82 and operate to provide an electrical connection. It is understood that the blocks 82 and pin receiving portions 84 may also have any other configuration. That is, the blocks 82 might be formed in another shape and/or the pin receiving portions 84 might be arranged in any other configuration on the blocks 82. It is also understood that any of these alternative embodiments could incorporate any of the various components described herein.

In a further alternative, the stackable blocks are secured in another fashion. That is, according to one embodiment, in the absence of the cam assembly, the blocks may be secured via a bolt that is disposed through a central hole in each of the stackable blocks 12 and the insertion end block 14. One example of such a central hole 60 is depicted in FIG. 8C. According to one embodiment, the bolt may be secured to the end block 16 via a mating feature. For example, the bolt may have a threaded end that mates with a threaded hole in the end block 16. Alternatively, any known components for securing such a bolt to an end block may be used. The bolt may be fabricated from a high strength biocompatible material such as stainless steel, a titanium alloy, a Co—Cr alloy such as MP35N, an Inconel alloy, or any other known high strength biocompatible material. In one implementation, the proximal portion of the bolt has a drive mechanism to allow for proper tightening on the assembly and may also have an over cap to minimize potential exposed surface crevices after assembly. In one embodiment, the bolt is the only feature for securing the blocks together. Alternatively, the bolt may be used in conjunction with the external clip 110.

Figure 10:
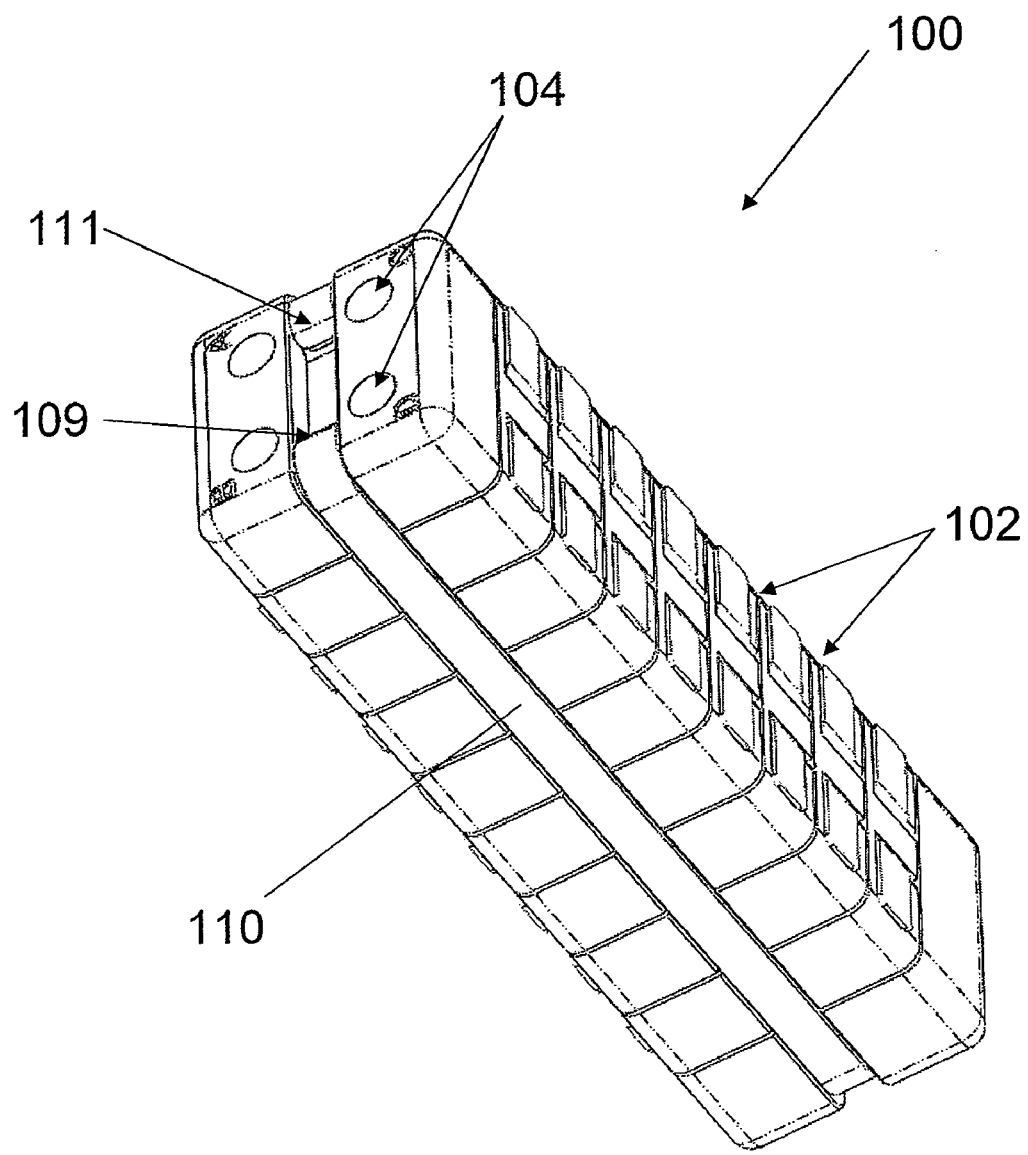
FIG. 10 depicts an electrical connection apparatus according to another implementation.

FIG. 10 depicts an electrical connection apparatus 100, according to another embodiment. This apparatus 100 provides for easy insertion and removal of contact pins. The apparatus 100 has four pin receiving portions 104 defined within the blocks 102 of the apparatus 100. As discussed above with the embodiment depicted in FIG. 1, the pin receiving portions 104 are disposed through almost the entire length of the device 100. A pin (not shown) may be inserted into each of the pin receiving portions 104 and once activated, will be placed in contact with each of the C-shaped contact points 108 (see FIG. 11A) as described below. As in the previous embodiment depicted in FIG. 1, each pin has internal wires or leads that are electrically connected to the circumferential contact areas of the pin, similar to areas 34 as shown in shown in FIG. 1.

FIG. 10 also depicts one embodiment for securing the stackable blocks 102. That is, the blocks 102 are secured with an external clip 110 that connects the end cap block 16 to the insertion end block 14. In one implementation, the clip 110 is a single U-shaped spring that has two ends. The first end is secured at a first attachment point 109 on the end block and the second end is secured at a second attachment point 111. The length of the U-shaped clip 110 runs along the outside of the device 100 and wraps around the other end block along a channel defined in the other end block, thereby securing the stackable blocks 102 together. Alternatively, the external clip 110 may be two C-shaped clips, each having a hook-like feature at each end of the clip. In this embodiment, there are two attachment points in each end block (instead of just one end block as shown in FIG. 10) such that one C-shaped clip 110 is disposed on one exterior side of the connector 100 and the other C-shaped clip is disposed on the opposite side and both are attached to the end blocks with the hook feature.

Figure 11A:
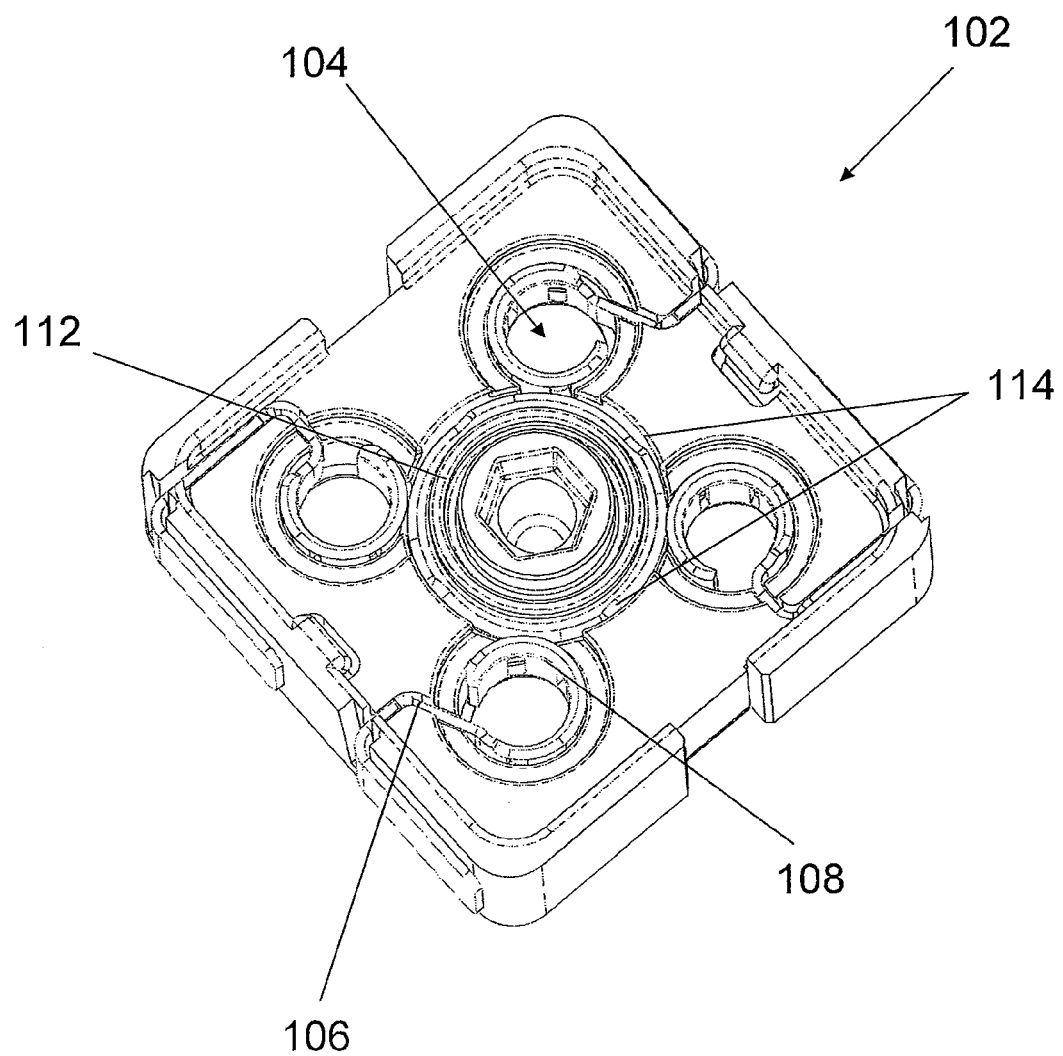

FIG. 11A depicts a block 102 of the apparatus depicted in FIG. 10. Like the blocks depicted in FIGS. 4A and 4B, block 102 has C-shaped contact portions 108 disposed within pin receiving portions 104. However, the C-shaped contact portions 108 in this embodiment differ from the C-shaped contact portions 28 described above with respect to FIGS. 3, 4A, and 4B. More specifically, the C-shaped contact portions 108 do not have an unconstrained diameter that is smaller than the OD of the pin. To the contrary, the natural configuration of the C-shaped contact portions 108 in this embodiment have a diameter that is greater than the OD of the pin.

Figure 12A:
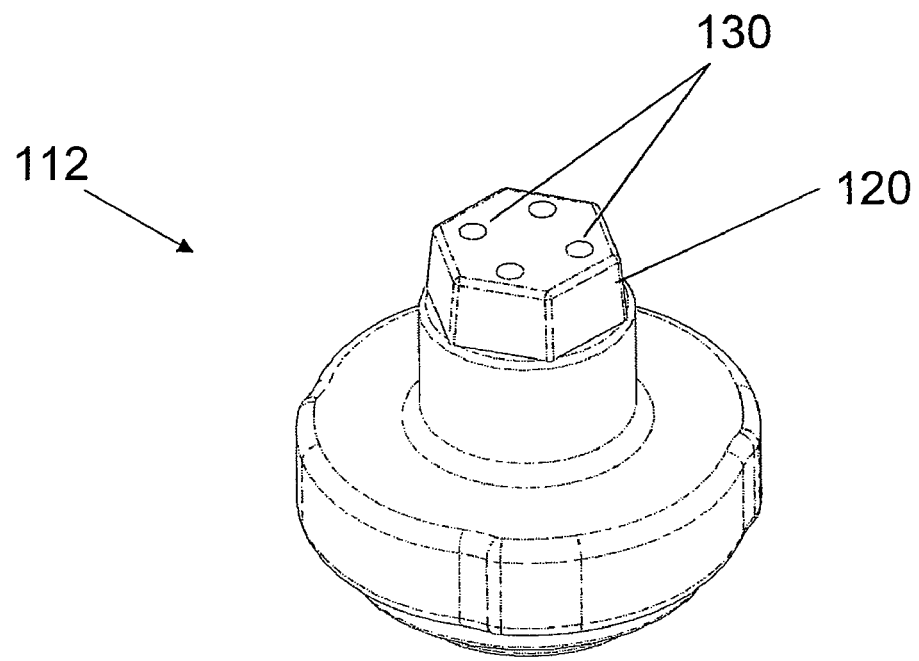
FIGS. 12A-B depict a first and second sides of a cam component.
Figure 12B:
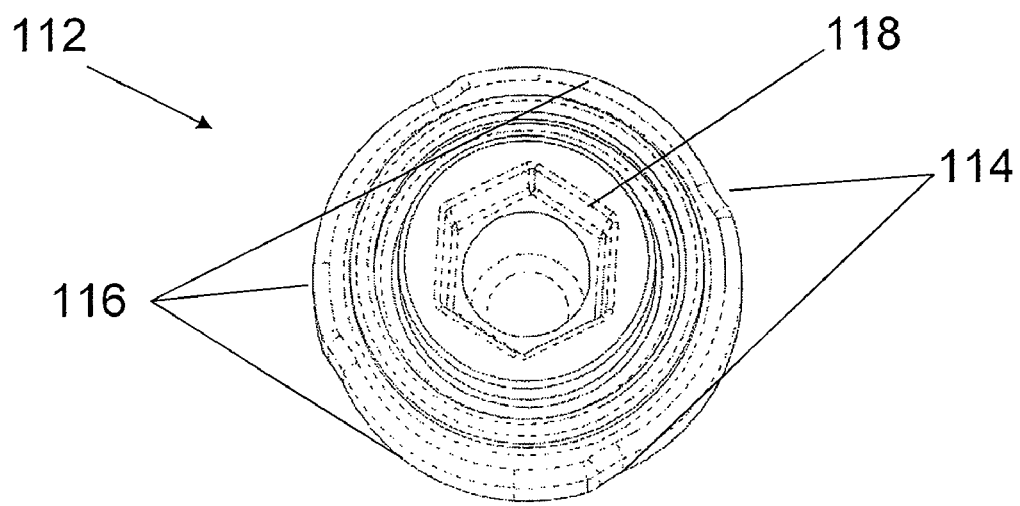

In addition, the block 102 has a cam component 112 disposed in a central portion of the block 102 such that the cam component 112 is in contact with each of the pin receiving portions 104. The cam component 112, which is depicted in further detail according to one embodiment in FIGS. 12A and 12B (which depict both sides of a cam component 112), has four indentations 114 and four contact portions 116 around the circumference of the component 112. In addition, the component 112 has a drive receiving component 118 on one side as shown in FIG. 12B and drive component 120 on the other side as shown in FIG. 12A. According to one embodiment, the drive receiving component 118 is an inset hexagon 118 and the drive component 120 is a coupleable hexagon drive component 120.

Each block 102 in this embodiment has a similar cam component 112 such that when the blocks 102 are connected to each other, the drive components 120 of each cam component 112 are inserted into the adjacent drive receiving component 118 on the adjacent block 102, thereby resulting in each of the cam components 112 in each of the blocks 102 being connected. In this embodiment, the connected cam components 112 may be turned using a tool 122 depicted in FIG. 13, e.g., a wrench such as a torque wrench.

Figure 13:
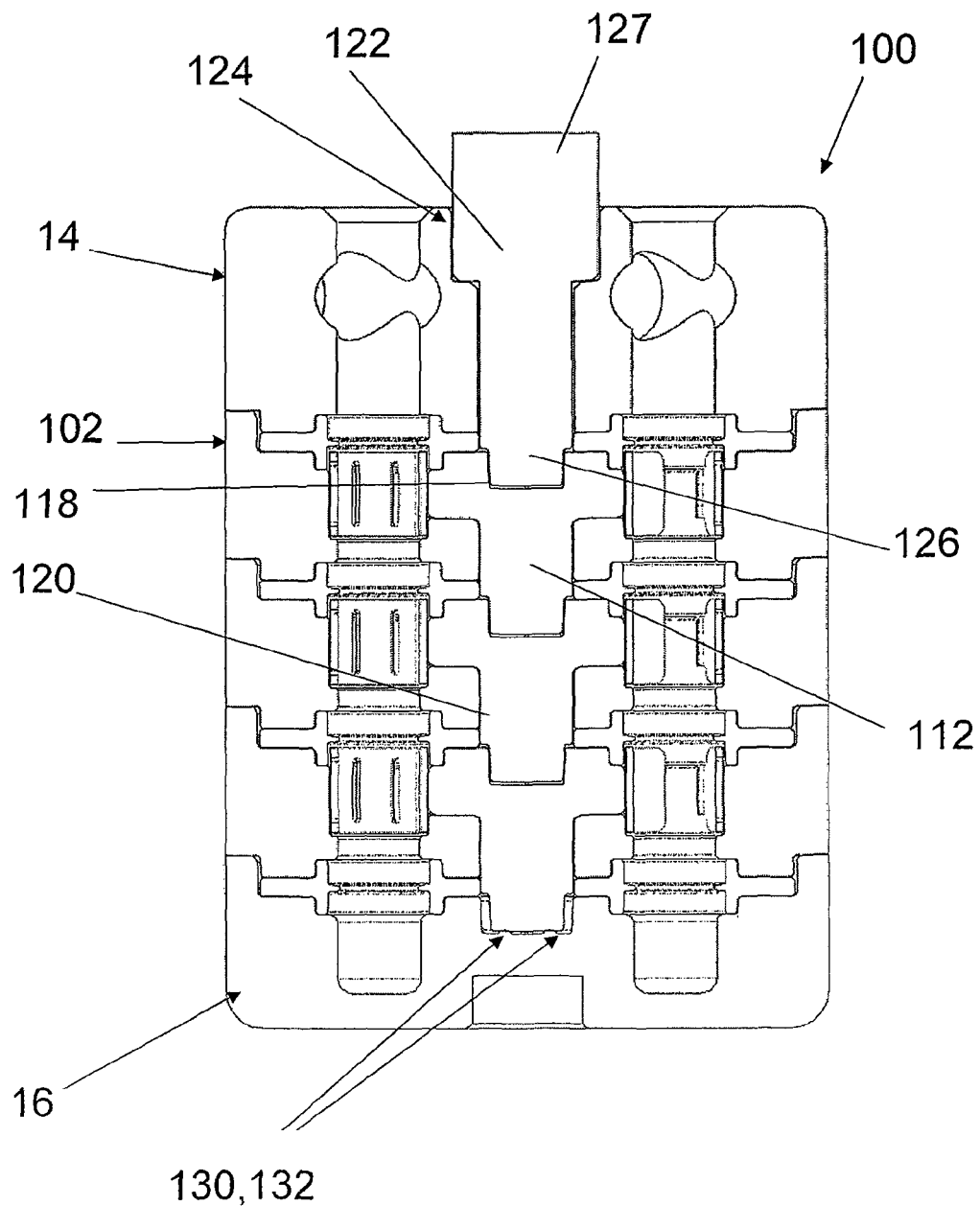
FIG. 13 depicts a cross-sectional view of the an electrical connection apparatus according to an alternative configuration.

According to the electrical connection apparatus 100 depicted in FIG. 13, the tool 122 is inserted through a central hole 124 defined in the end block 14 and positioned into the drive receiving component 118 of the cam component 112 of the block 102 connected to the end block 14, whereby the tool 122 may be used to turn the connected cam components 112.

In one embodiment, the tool 122 has on its distal end 126 (the end that contacts the drive receiving component 118) certain features that may improve torque transmission. According to one embodiment, the feature may be a shaped end (such as a hexagonal shape, for instance) that is engageable with the drive receiving feature 118 of the cam 112. Additionally, in one implementation, the proximal end 127 of the tool 122 may have screw drive features (such as slots, hex, torx, etc.), external knurling, increased circumference flange, or any other known features for improving torque transmission. In one implementation, the proximal end 127 of tool 122 is configured as a hex driver.

As best depicted in both FIGS. 11A-C, it is understood that the configuration of blocks 102 is slightly different from the blocks depicted in FIGS. 4A and 4B. That is, the slots in blocks 102 have a different configuration to accommodate the slightly different configuration of the electrical connection contacts. According to one embodiment, this configuration allows for a central hole defined in each of the assembly blocks 102.

In use, the cam component 112 provides for the easy insertion and removal of the pins. That is, when the cam component 112 is rotatably disposed such that the four indentations 114 are adjacent to the pin receiving portions 104 (the "insertion position"), each C-shaped contact portion 108 is disposed at its largest diameter, which is greater than the OD of a pin. Thus, when the cam component 112 is in the insertion position, a pin may easily be inserted into or removed from a pin receiving portion 104 while experiencing little or no frictional contact with the C-shaped contact portion 108. Thus, the pin may be inserted or removed with little or no force.

In contrast, when the cam component 112 is rotatably disposed such that the four contact portions 116 are adjacent to the pin receiving portions 104 and in contact with the C-shaped contact portions 108 (the "contact position"), each C-shaped contact portion 108 is urged into contact with the pin by the force of the contact portion 116 of the cam component 112, thereby resulting in electrical contact between the C-shaped contact portion 108 and the pin. An example of the contact position is depicted in FIG. 11A. In one embodiment, the C-shaped contact portion 108 is in electrical contact with the circumferential contact area of the pin similar to the contact area 34 depicted in FIG. 1.

Thus, the tool 122 may be used to turn the connected cam components 112, thereby moving the C-shaped contacts 108 between the insertion position and the contact position. That is, the tool 122 may be used to turn the cam components 112 such that the contact portions 116 are positioned in contact with the C-shaped contacts 108, thereby urging them into contact with the pins. In addition to establishing a stable electrical contact interface between the C-shaped contacts 108 and the pin, the pressure of the C-shaped contacts 108 against the pin acts to prevent movement of the pin or otherwise secure the pin in its position within the pin receiving portion 104.

Further, the tool 122 may be used to turn the cam component 112 such that the four indentations 114 are in contact with the four C-shaped contacts 108, thereby allowing each C-shaped contact 108 to expand and to return to the insertion/withdrawal position.

In certain embodiments, after the cams 112 are set to the appropriate position, the tool 122 may be removed and replaced with a lower profile cap. Alternatively, no cap is provided.

According to one implementation, the combined force of the C-shaped contacts 108 in contact with the pin creates a sufficiently large mechanical force on the pin such that the pin is not easily dislodged or otherwise disconnected via physical movement of the device 100 or pin. As such, the device 100 may withstand outside physical forces, including shaking, twisting, and/or other such forces, without disrupting the connection between the pins and the contact portions 108 as a result of the stable configuration of the contact adjustment component 112 and contact portions 108. As an example, this stability may, in some embodiments, allow a patient requiring such a device 100 to be more physically active than is possible with known devices. In another embodiment, the apparatus 100 may also have a mechanical fastening port (not shown) similar to that described above with respect to FIG. 1, thereby providing further stability.

In the embodiment shown in FIG. 13, an apparatus may provide a tactile response to rotation of the cam component 112 such that a user may properly position the cam component 112. In one embodiment, the tactile response is provided by mated detent features disposed on the drive component 120 of the cam component 112 as shown in FIG. 12A and on the portion of that end block 16 that contacts the cam component 112 as shown in FIG. 13. More specifically, the drive component 120 has female detent features 130 shaped as hemispheres formed into the end of the component 120. Further, the end block 16 has male detent features 132 shaped as hemispheres that may mate with the female detent features 130. In use, as the cam component 112 is turned, the user may feel the mating and unmating of the detent features and thereby may easily determine the position of the cam component 112. According to one embodiment, the detent features 130, 132 are positioned such that the features mate when the cam component 112 is positioned in the contact position, such that the tactile response of the detent features 130, 132 mating indicates to the user that the cam component 112 is in the contact position.

In an alternative embodiment, a tactile response is achieved through a set of small indentations (not shown) disposed on the contact portions 116 of the cam component 112. These indentations are much smaller and shallower than the indentations 114 and are placed at the optimal contact points 116 on the cam component 112. These indentations provide a tactile response to the user, indicating that the cam component 112 is in the contact position.

In a further embodiment, a visual method of positioning the cam component 112 is provided. In this embodiment, alignment markers are placed on the end block 14 and the top of the cam tool 122.

Figure 14A:
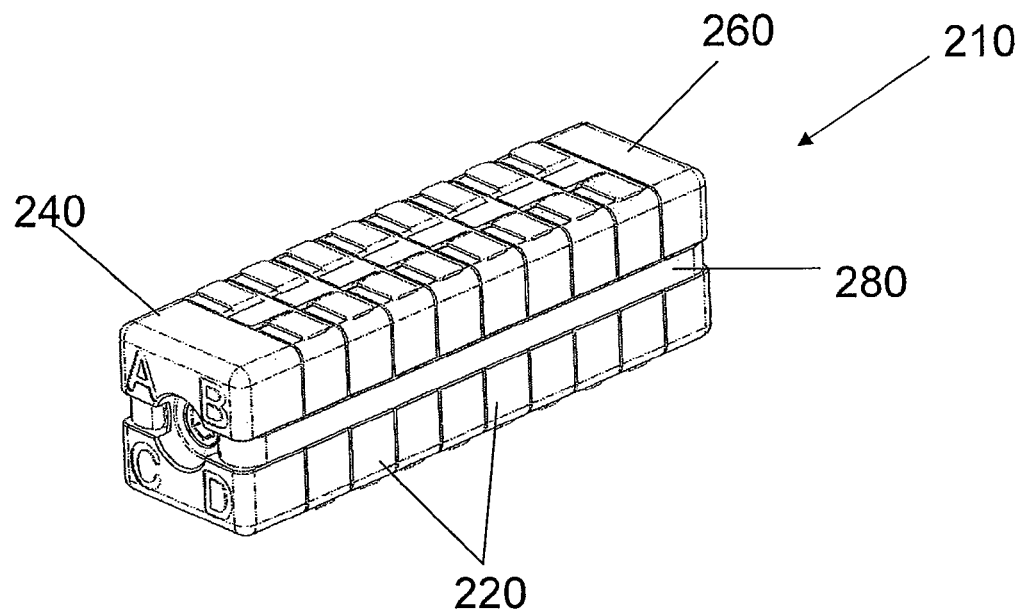
FIGS. 14A-B depict a first and second perspective view of another electrical connection apparatus according to certain implementations.
Figure 14B:
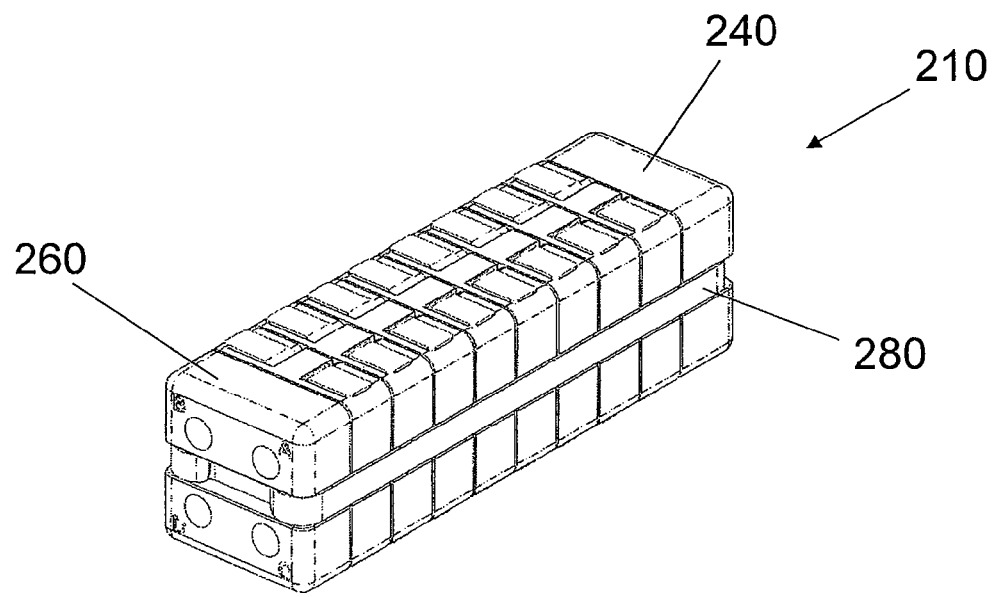

FIGS. 14A-B depict a first and second perspective view of another electrical connection apparatus 210, according to certain implementations. The electrical connection apparatus 210 includes stackable blocks 220 arranged between end blocks 240, 260. The assembly of blocks 220, 240 and 260 may be held together by external spring clip 280 or by a U-shaped clip (not shown) with the terminal ends of the U-shaped clip terminating at end block 240. Electrical connection apparatus 210 may connect two implantable components, e.g., leads and a medical device, in the manner discussed above in relation to the electrical connection apparatus 10 of FIG. 1. However, according to the presently described implementation, the electrical connection apparatus 210 is configured so that cam action is initiated from one end, e.g., the end corresponding to end block 240, and pins enter from another end of apparatus 210, e.g., the end corresponding to end block 260. This embodiment may provide certain advantages because, due to the small allowable space for active implantable devices and the small sizing of the electrical connectors, placing leads at one end of the device and rotating the cam at the opposite end may reduce the chance of entanglement between the leads and the rotating mechanism, hands, tool, torque wrench, etc., during manual rotation or operation of the cam.

FIGS. 15A-F depict perspective views of a first and second side of a first end block 240, a stackable block 220 and a second end block 260 of apparatus 210 shown in FIGS. 14A-B.

Figures 15A, 15B:
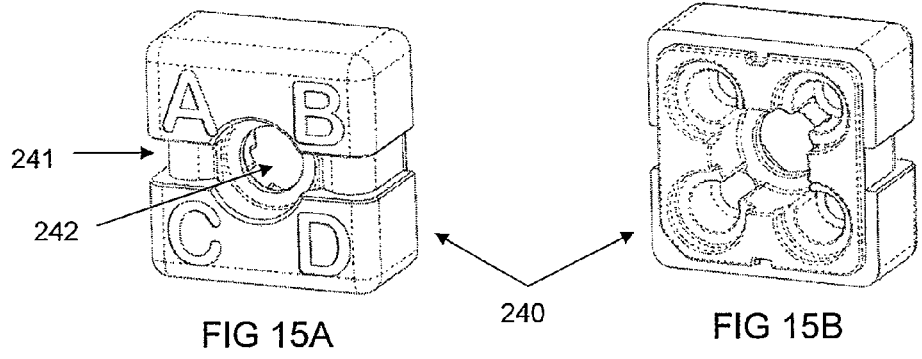
FIGS. 15A-F depict perspective views of a first and second side of a first end block, a stackable block and a second end block of the apparatus of FIGS. 14A-B.
Figures 15C, 15D:
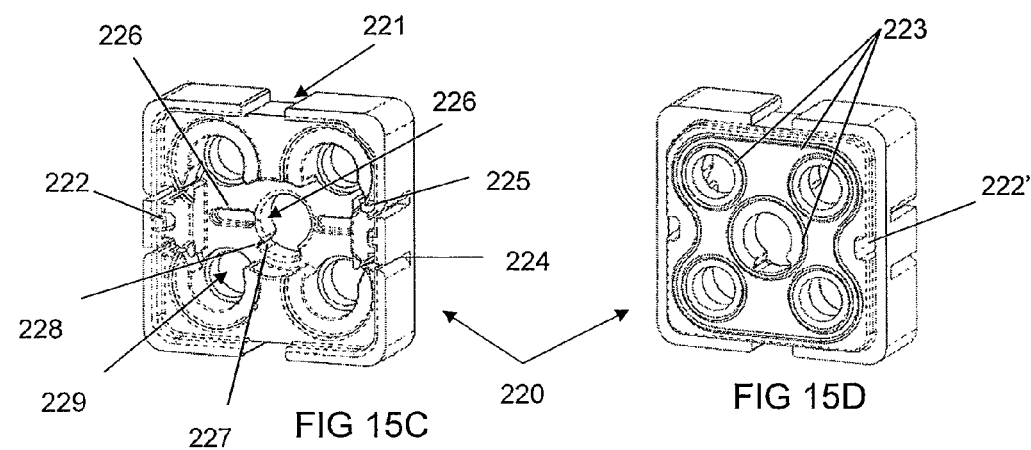

In FIGS. 15A-B, end block 240 is configured with grooves 241 on opposite sides of the block for accommodating external clip 280, an opening 242, which provides access to a cam or other adjustment component (not shown) situated in an adjacent stackable block 220, and receivers 243 for receiving retaining clips 222 arranged on stackable block 220 (shown in FIG. 15C). End block 240 serves as an access point for accessing a cam or other adjustment component arranged on the interior of the assembled apparatus 210 and may have a configuration similar to insertion end block 14 of FIG. 1, except that end block 240 does not include the pin receiving portions described in relation to FIG. 1.

FIGS. 15C-D depict perspective views of a first and second side of a stackable block 220. In FIGS. 15C-D, block 220 includes grooves 221, retaining clip 222, receivers 222' for retaining clips 222, knife edges 223, slots 224, potting pockets 225, cam receiving portion 226, cam detents 227, cam hard stops 228 and pin receiving portions 229. Grooves 221 on opposite sides of the block accommodate spring clip 280 and may facilitate maintaining the desired positioning of spring clip 280 on the assembled apparatus 210. Retaining clips 222 arranged near the periphery of an interior facing portion of block 220 may facilitate holding seals 250 in place (See FIG. 21A) and may aid in assembly of adjacent blocks, e.g., adjacent end blocks 240, 260 or other stackable blocks 220. For example, during assembly, retaining clips 222 may engage with receivers 222' arranged near the periphery of an interior facing portion of another block 220 or from receivers 243 arranged near the periphery of an interior facing portion of an adjacent end block 240. Knife edges 223 provided on stackable blocks 220 may facilitate providing a seal between seal plate 250 and stackable blocks 220.

Each stackable block includes four slots 224 for providing an electrical connection contact (not shown) access to the exterior of the block 220. Four potting pockets 225 are arranged in an area proximate the slot 224 and may accommodate an epoxy or other polymeric resin, which may seal slots 224 and prevent moisture ingress to the interior of apparatus 210. Cam receiving portion 226 is defined by interior walls of stackable block 220 and is configured to receive a cam (not shown) or other adjustment component and includes cam hard stops 228 that cooperate with the cam 330 and serve as stop points for the cam rotating from a locking or contact to an unlocking or insertion position. Cam detents 227 are arranged adjacent the cam hard stops 228 and serve as an indicator to a user rotating the cam that the cam has reached a locking or contact position or an unlocking or insertion position. Four pin receiving portions 229 are each configured to accept a pin (not shown) and are defined by interior walls of stackable block 220.

Figures 15E, 15F:
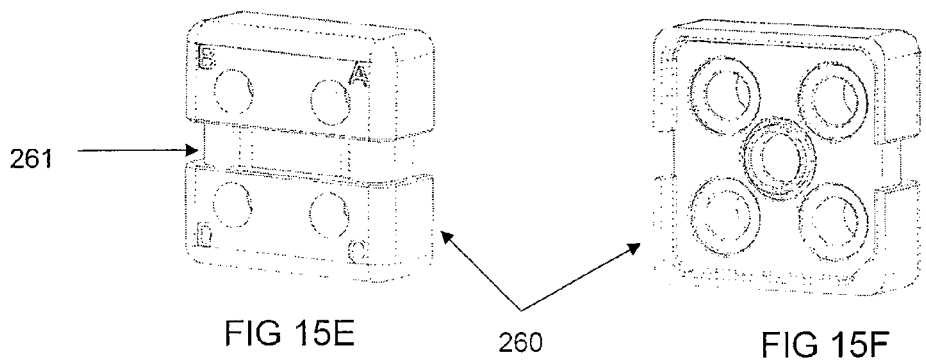

FIGS. 15E-F depict perspective views of a first and second side of a second end block 260, which may be configured similar to end cap block 16 described in relation to FIG. 1, except that end block 260 may include pin receiving portions and/or fastening ports similar to those provided in insertion end block 14. End block 260 also includes a groove 261 for accommodating external spring clip 280 or a U-shaped spring that would traverse exterior of the second end block along the length of the groove.

Figure 16A:
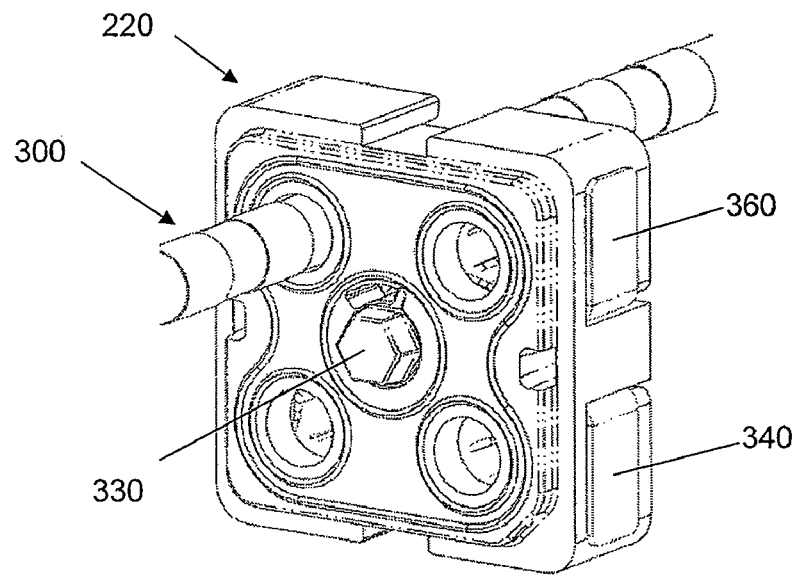
FIGS. 16A-B depict perspective views of a first and second side of a stackable block with a segmented contacting pin in place.
Figure 16B:
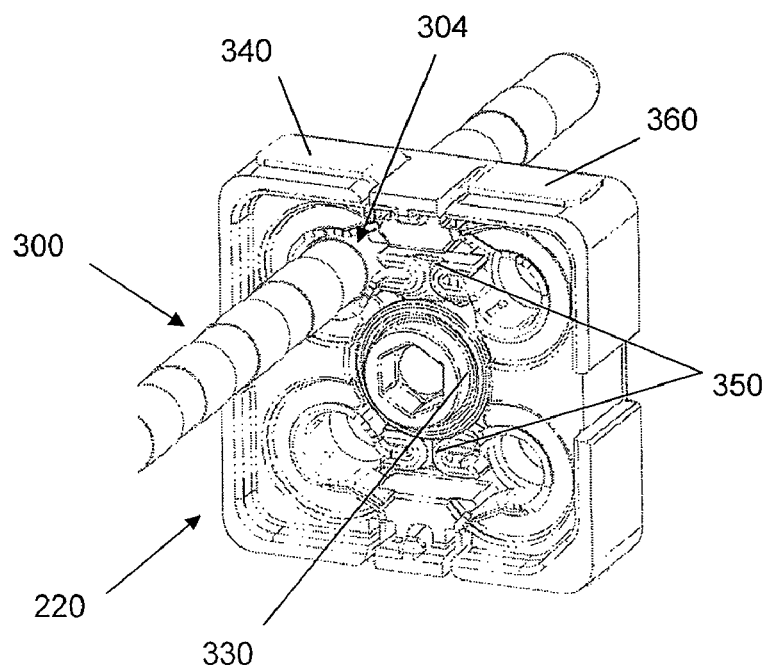

FIGS. 16A-B depict perspective views of a first and second side of the stackable block 220 with a pin 300 inserted through the block. FIG. 16A depicts a drive component of cam 330 in an insertion position. FIG. 16B depicts the assembly from the back side and the cam 330 with the drive receiving component is set in the open or initial insertion position.

Figure 17A:
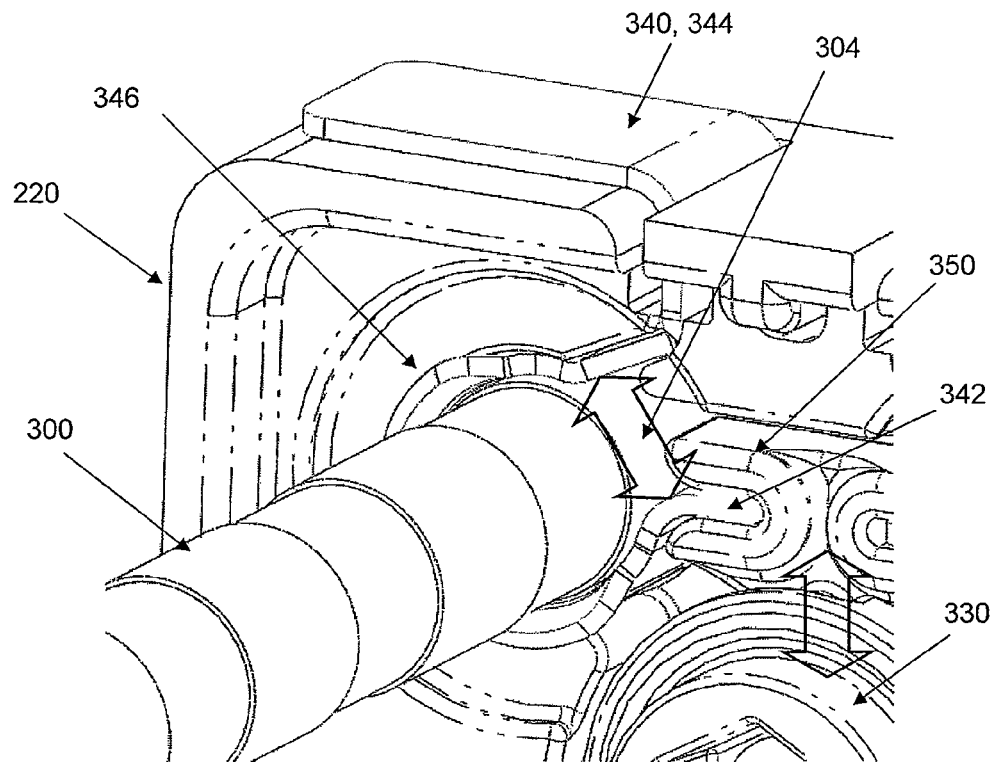
FIGS. 17A-B depict perspective views of the slider and contact in both the insertion and contact position relative to the pin.

FIG. 17A depicts one of the contact assemblies in the unlocked position. The cam 330 is loosely coupled to a slider 350, which is mechanically engaged to an electrical connection contact 340 via a tab 342 (see FIG. 19A). In the unlocked position, slider 350 is in a lowered position relative to the periphery of stackable block 220 and loosely engaged with electrical connection contact 340. Electrical connection contact 340 is in a relaxed state, and as a result, pin 300 arranged in block 220 may be slidable through the C-shaped connection 346 in the contact 340. Thus, in FIG. 17A, the cam 330, slider 350 and tab 342 are in an insertion position, and a pin may be inserted into or removed from a pin receiving portion 229 while experiencing little or no frictional contact with the C-shaped contact portion 346, resulting in the pin being insertable or removable with little or with zero insertion force.

Figure 17B:
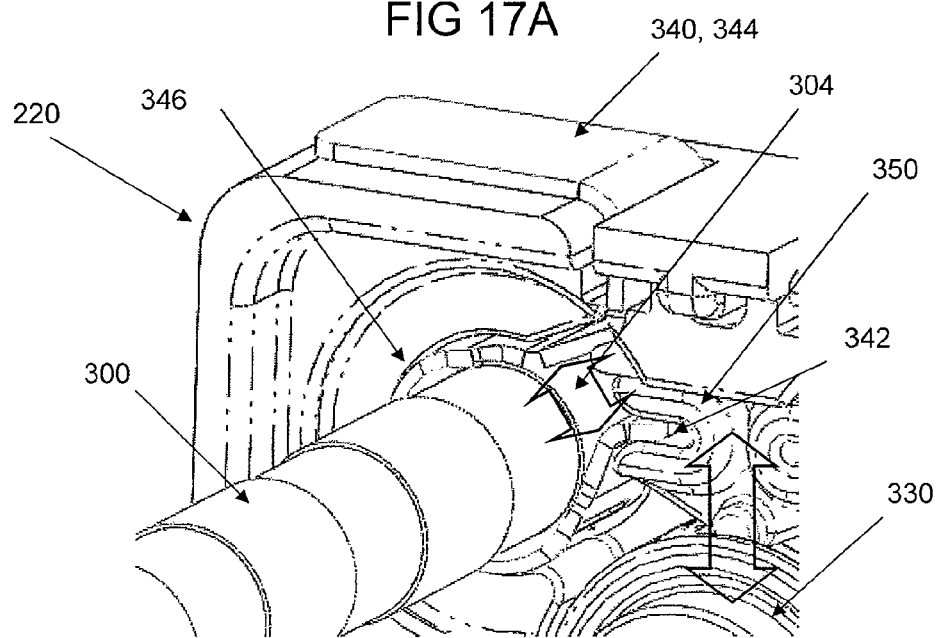

In FIG. 17B, a first side of the contact assembly is shown in its locked position. Cam 330 has raised the position of slider 350 and C-shaped contact portion 346 is clinched around pin 300 at an electrically-isolated circumferential contact 304. As a result, when cam 330 is in a locked position, pin 300 is locked into position about its circumferential contact 304 by the reduction of the circumference of the C-shaped portion of electrical C-shaped contact 346. This action completes the electrical path from the external contacts 344 through the C-shaped contact 346 to the isolated pin contact 304 to the internal pin lead 30 (see FIG. 1). When four pins 300 are provided in apparatus 210, each slider 350 is responsible for raising the position of two tabs 342, 362 (see FIGS. 19A and B), which in turns clinches two of the four pins 300. Providing sliders 350 that engage with tabs 342, 362 to cause the C-shaped contacts 346 to tighten around and couple to pins 300 in response to cam action, according to the present implementation, may reduce or prevent buckling of the C-shaped portion 346, 366 of the electrical connection contacts 340, 360.

According to FIG. 17B, in addition to establishing a stable electrical contact interface between the C-shaped contacts 346 and the pin 300, the pressure of the C-shaped contacts 346 against pin 300, due to the positioning of slider 350 in a contact position, may prevent movement of the pin or secure the pin in its position within the pin receiving portion 229. The force of the C-shaped contact 346 in contact with the pin may provide a sufficiently large mechanical force on the pin such that the pin may not be dislodged or dislodged easily, or otherwise disconnected via physical movement of the device 210 or pin 300. Thus, the device 210 may withstand outside physical forces, including shaking, twisting, and/or other such forces, without disrupting the connection between the pins and the contact portions 346 as a result of the stable configuration of the cam 330, slider 350 and tab 342.

Figure 18A:
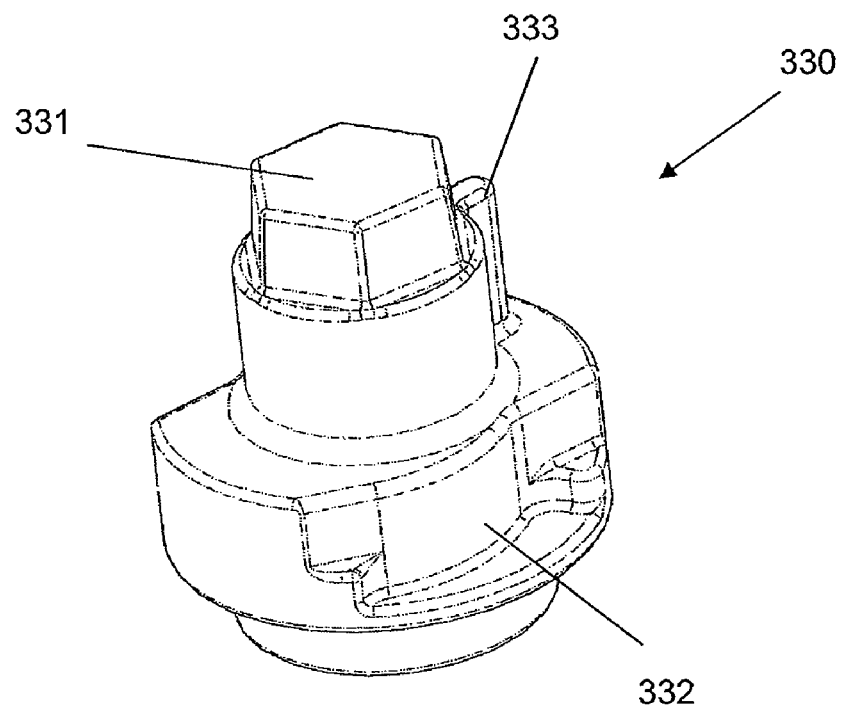
FIGS. 18A-B depict perspective views of a first and second side of a cam according to certain implementations.
Figure 18B:
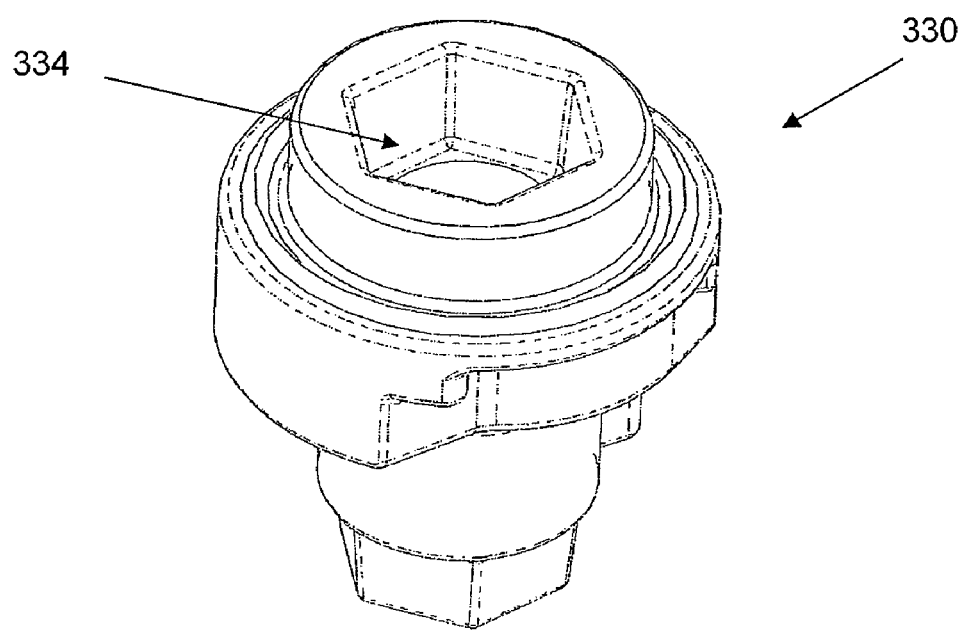

FIGS. 18A-B depict perspective views of a first and second side of cam 330. Cam 330 includes a drive component 331, eccentric paths 332 for sliders 350, detent feature 333 and a drive receiving component 334. In FIG. 18A, the drive component 331 having a tapered hexagonal male portion is configured such that it fits into an adjacent cam by way of a complementary drive receiving component 334 having a tapered hexagonal female receiving configuration. When cam 330 is arranged in block 220, the drive component 331 protrudes beyond the an exterior surface of block 220, see e.g., FIGS. 16A and 17A. Eccentric paths 332 for slider 350 may be configured so that when cam 330 is arranged in block 220, eccentric paths 332 loosely couple to the sliders 350 when in an insertion or unlocked position, and moves sliders 350 up or down when in a contact or locked position. Detent feature 333 engages with cam detents 227 of block 220 when cam 330 is moved to either a locked or an unlocked position. When detent feature 333 reaches one of the cam detents 227, a user exerting torque, e.g., by way of a tool such as a wrench or a torque wrench, on the cam assembly may feel detent feature 333 engage with the cam detent. Where a user continues to exert torque on the cam assembly after the detent feature 333 engages with cam detent, detent feature 333 may abut an adjacent cam of the pair of cam hard stops 228 provided on block 220 preventing cams from further rotational movement. In use, cams 330 from adjacent blocks 220 interlock via the drive and drive receiving components 331, 334, respectively. Accordingly, actuation of a cam 330 arranged in a stackable block 220 adjacent to end block 240 results in actuation of each of the cams 330 arranged in the electrical connection apparatus 210. Furthermore, because detents 227 and hard stops 228 in stackable block 220 cooperate with cam 330, initiating cam action with a torque wrench may provide for precise engagement and rotation of cams 330 within electrical connection apparatus 110.

FIGS. 19A-B depict perspective views of electrical connection contact 340, 360 for use on a left and a right side of the stackable block 220. FIGS. 20A-B depict perspective views of a first and second side of a slider 350 for use with the stackable block 220 and include recesses 351 and 352 for engaging with electrical connection contact 340, 360. According to certain implementations, sliders 350 may be constructed of plastic, ceramic, other insulating material, or may be coated with an insulating material.

With reference to FIG. 19A, a left side electrical connection contact 340 includes tab 342 for engaging with slider recess 351, exterior contact portion 344 for contacting an external device and for aligning along an exterior length of the stackable block 220, and C-shaped interior contact portion 346 for aligning with pin receiving portion 229 and for contacting pin 300. In FIG. 19B, a right side electrical connection contact 360 includes tab 362 configured for engaging with slider recess 351, exterior contact portion 364 for contacting an external device, and C-shaped interior contact portion 366 for aligning with pin receiving portion 229 and contacting pin 300. Tab 342, 362 provides slider recess 351 with a desirable length of the electrical connection contact 340, 360 such that the contact may be moved from an insertion to a contact position as a result of an upward or downward movement of the slider 350. Electrical connection contacts 340, 360 may also include features described above in relation to the electrical connection contacts of FIGS. 3A-B, 5A-G and 11.

Figures 21A, 21B:
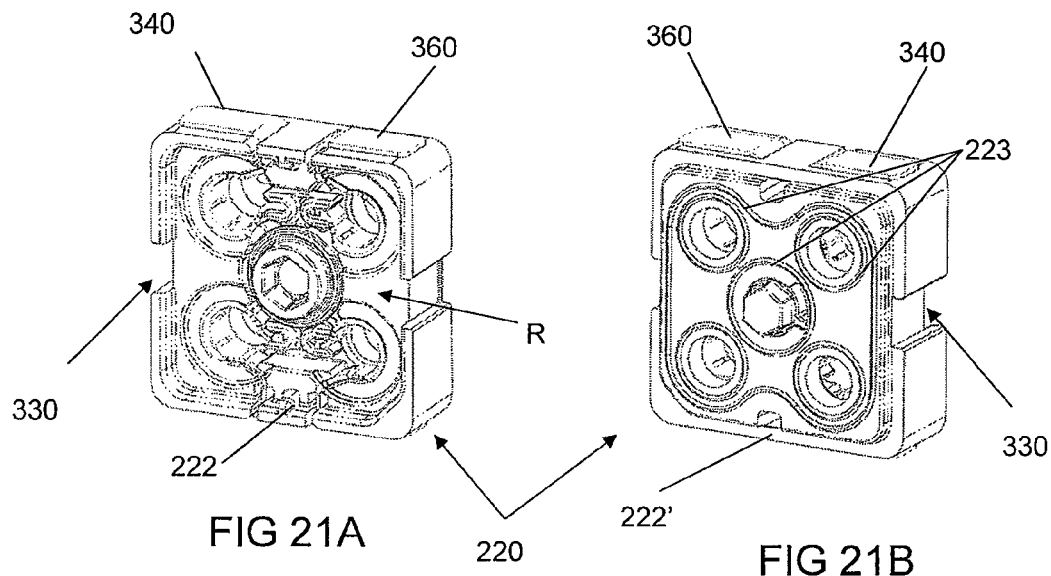
FIGS. 21A-B depict perspective views of a first and second side of the stackable block with a seal plate.
Figures 22A, 22B:
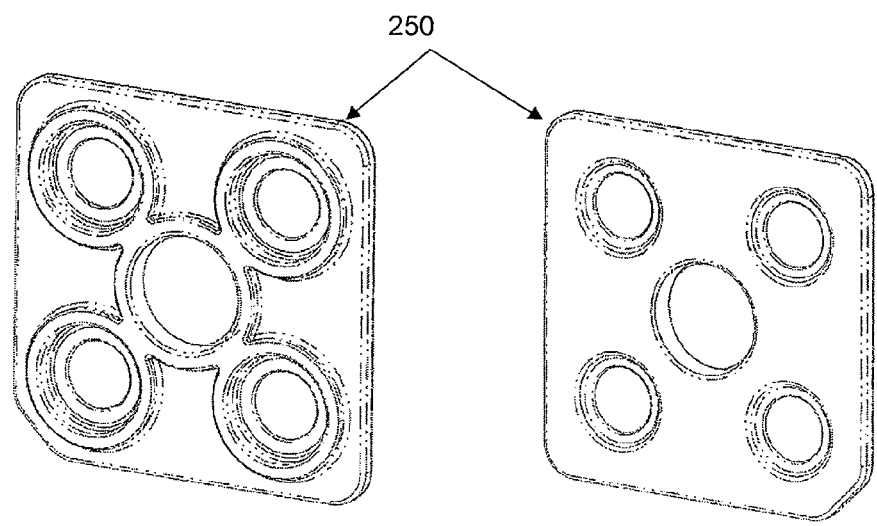
FIGS. 22A-B depict perspective views of a first and second side of the seal plate depicted in FIGS. 21A-B.

FIGS. 21A-B depict perspective views of a first and second side of the stackable block 220. FIGS. 22A-B depict perspective views of a first and second side of a seal component 250, which may be arranged on stackable block 220 at a position corresponding to the recessed portion R of seal block 220 depicted in FIG. 21A. Assembled electrical connection apparatus 210 (FIGS. 14A-B) may be provided with a seal component 250 between each block, e.g. between end block 240 and stackable block 220, between stackable blocks 220, and between stackable block 220 and end block 260 in order to prevent biological fluids from contacting pins 300, for example. In addition, stackable blocks 220 associated with the presently described apparatus 210 include clips 222, which may facilitate holding seal component 250 in place as well as engage with receivers 222', as shown in FIG. 21B. Moreover, knife edges 223 provided on stackable block 220 in the areas corresponding to the cam receiving portion 226, pin receiving portions 229, and an area surrounding each of the cam and pin receiving portions. Knife edges 223 may mate with vertical seal portions provided on seal component, which are shown and described in relation to FIG. 7.

Figure 23A:
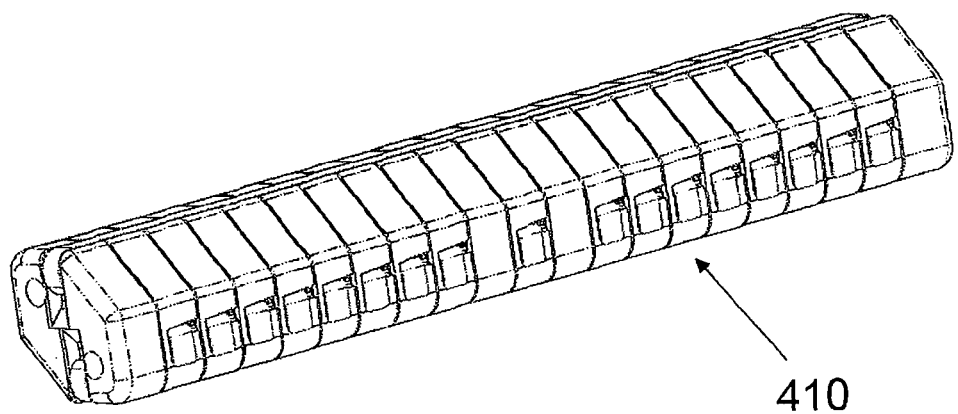
FIGS. 23A-B depict perspective views of a first and second perspective view of another electrical connection apparatus having a two pin configuration.
Figure 23B:
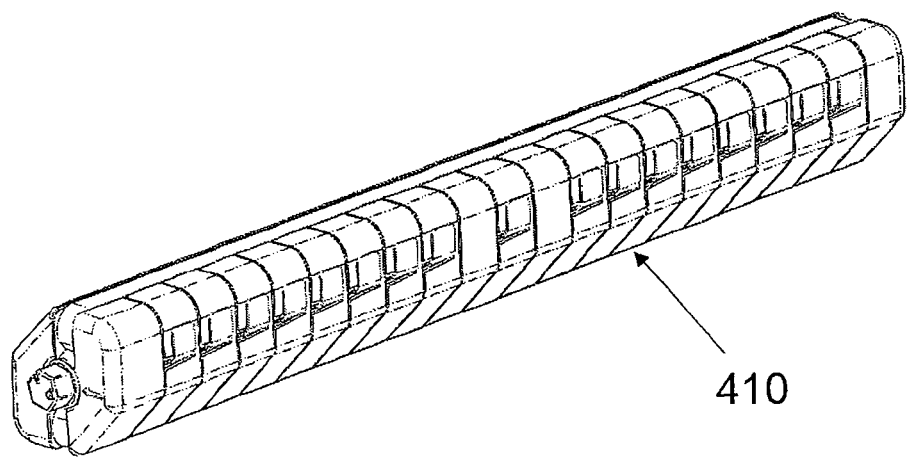

FIGS. 23A-B depict a first and second perspective view of another electrical connection apparatus 410 having a two pin configuration. Electrical connection apparatus 410 may otherwise be configured in a manner similar to that of electrical connection apparatus 10, 80, 100, and 210.

In certain implementations, all or a portion of electrical connection apparatus 10, 80, 100, 210 and 410 may be overmolded in silicone or another polymer in order to reduce or eliminate the chance of moisture ingress. In addition, in certain implementations, pin 20 and pin 300 may have a variety of diameters and configurations. For example, pins coupled to leads that deliver electrical pulses may be larger than pins coupled to sensing leads. Accordingly, the pin receiving portions of apparatus 10, 80, 100, 210 and/or 410 may be configured to accept a pin having a desirable cross-section or configuration.

Figure 24:
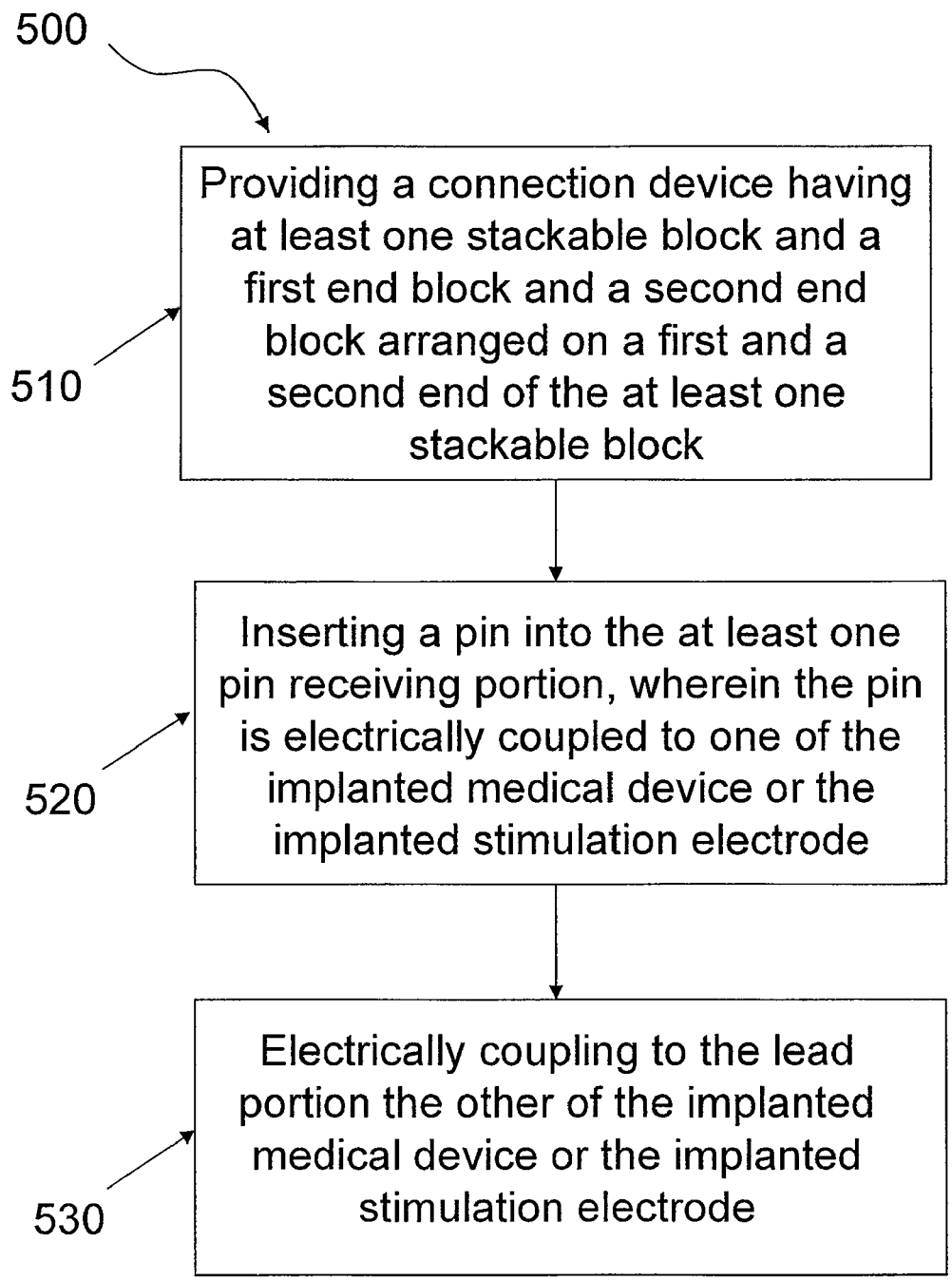
FIG. 24 is a flowchart of a method for electrically connecting an implanted medical device and an implanted stimulation electrode.

FIG. 24 is a flowchart of a method (500) for electrically connecting an implanted medical device and an implanted stimulation electrode according to the present invention. According to FIG. 24, method (500) includes providing (510) a connection device having at least one stackable block and a first end block and a second end block arranged on a first and a second end of the at least one stackable block, where each of the at least one stackable block includes at least one pin receiving portion, and at least one electrical connection contact. Method (500) also includes inserting (520) a pin into at least one pin receiving portion such that the pin is electrically coupled to an implanted medical device or to an implanted stimulation electrode, and electrically coupling (530) to the lead portion the other of the implanted medical device or the implanted stimulation electrode.

According to certain embodiments, the electrical connection apparatus passageway through which the proximal end of the lead must pass, with its exposed conductive surfaces in segments along its longitudinal axis, has a series of actively engageable seals or barriers alternating longitudinally with the conductive surfaces in the receptacle. When engaged, the active seals block the incursion of fluid along the lead's path, and prevent the migration of fluid from the region of one conductive surface in the receptacle to any other, and in the instance where there are already existing fluid bridges between conductors, forces the fluid out and breaks the electrical pathway.

Figure 25:
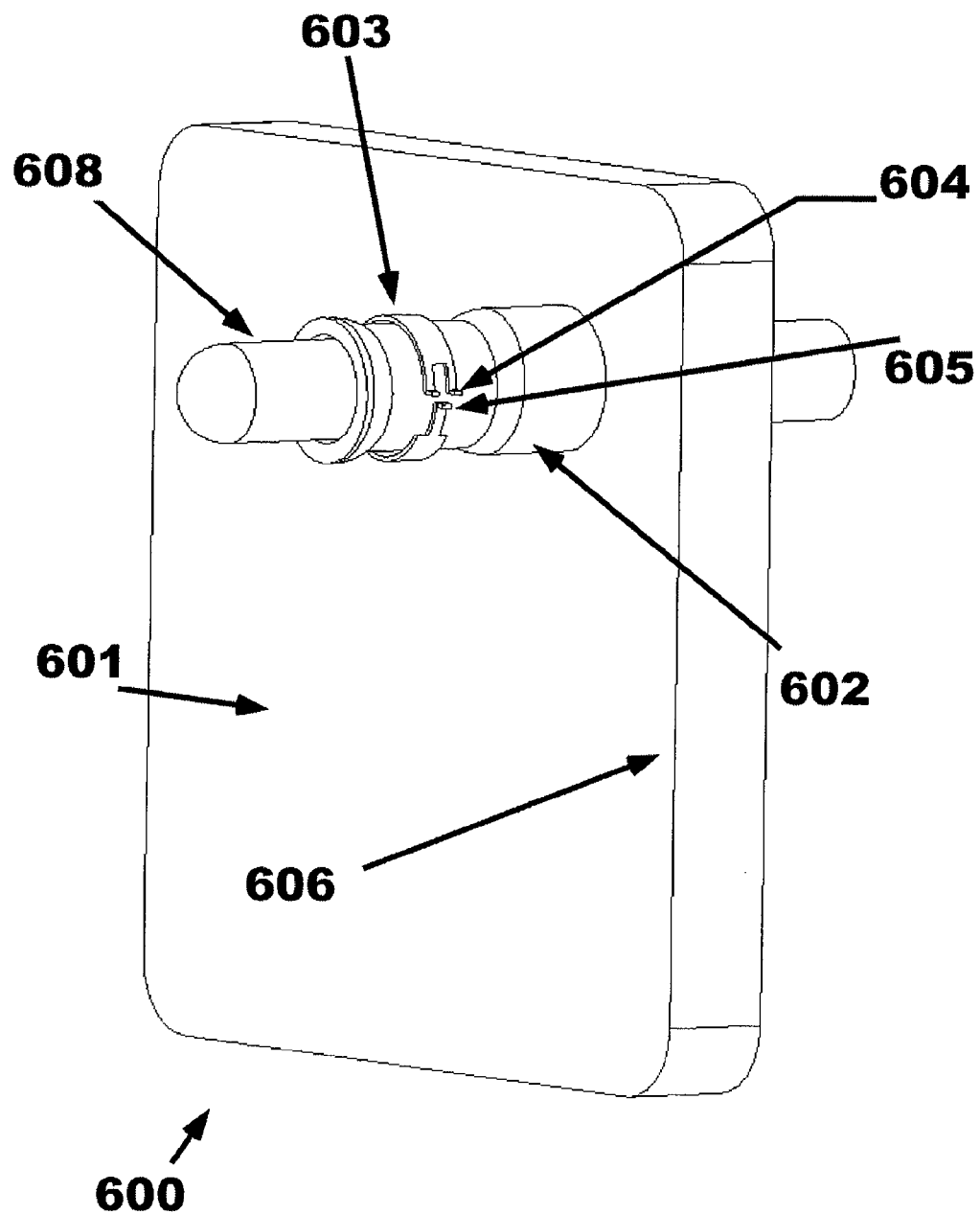
FIG. 25 is an isometric view of an active seal, according to certain embodiments.

FIG. 25 is an isometric view of an active seal, according to certain embodiments. A single lead lumen is shown for clarity; but a plurality of lead lumens may also be provided in a single seal. The figure depicts a fluid seal 600 with a substantially planar body 601. The perimeter 606 of the body 601 may be captured and compressed to form a boundary seal. The seal incorporates a cylindrical extension, or seal tube 602, which has a lumen defining a pin receiving portion with diameter just large enough to permit passage of a lead 608 with little or no clearance. According to certain embodiments, the seal tube 602 is surrounded at one point by a metallic ring or cinch 603 that can be reduced in diameter in order to reduce the diameter of the seal tube 602 around the lead 608. According to FIG. 25, the cinch 603 includes fixed position tabs 604 at one terminal end, which are captured by part of the housing of the connector block (see, e.g., FIG. 27A). The other, opposite end of the cinch 603 comprises a moveable tab or tabs 605, which is/are engaged by a moving a mechanism pushed by a cam (see, e.g., FIGS. 27A-27C). Moveable tab 605 is forced towards and past fixed position tabs 604, thus reducing the diameter of the cinch 603. This compresses the material of the seal tube 602, which then is pressed tightly to the outer surface of the lead 608. Of course, both tabs may be movable towards and away from each other in order to constrict and relax the cinch 603.

Figure 26:
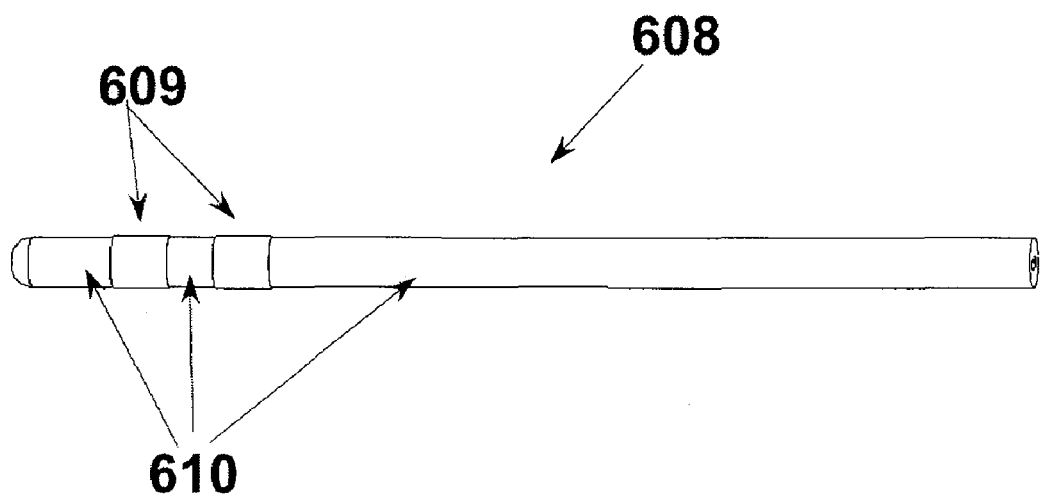
FIG. 26 depicts a proximal end of an implanted lead.

FIG. 26 depicts a proximal end of an implanted lead 608. The body of the lead comprises an insulating flexible polymer with internal conductors. At the proximal end, the conductors are exposed by means of external metal contacts such as rings 609, with sections of insulator 610 between them to isolate them from each other. This proximal end of the implanted lead, commonly called a "pin" is the portion of the lead which enters the connector block. Dummy pins are also used which have the same diameter and proximal length as the lead pin. These dummy pins fit into the seal tubes 602 of FIG. 25, when the surgical scenario does not present with a sufficient number of lead pins to fill all the seal tubes on a device.

Figure 27A:
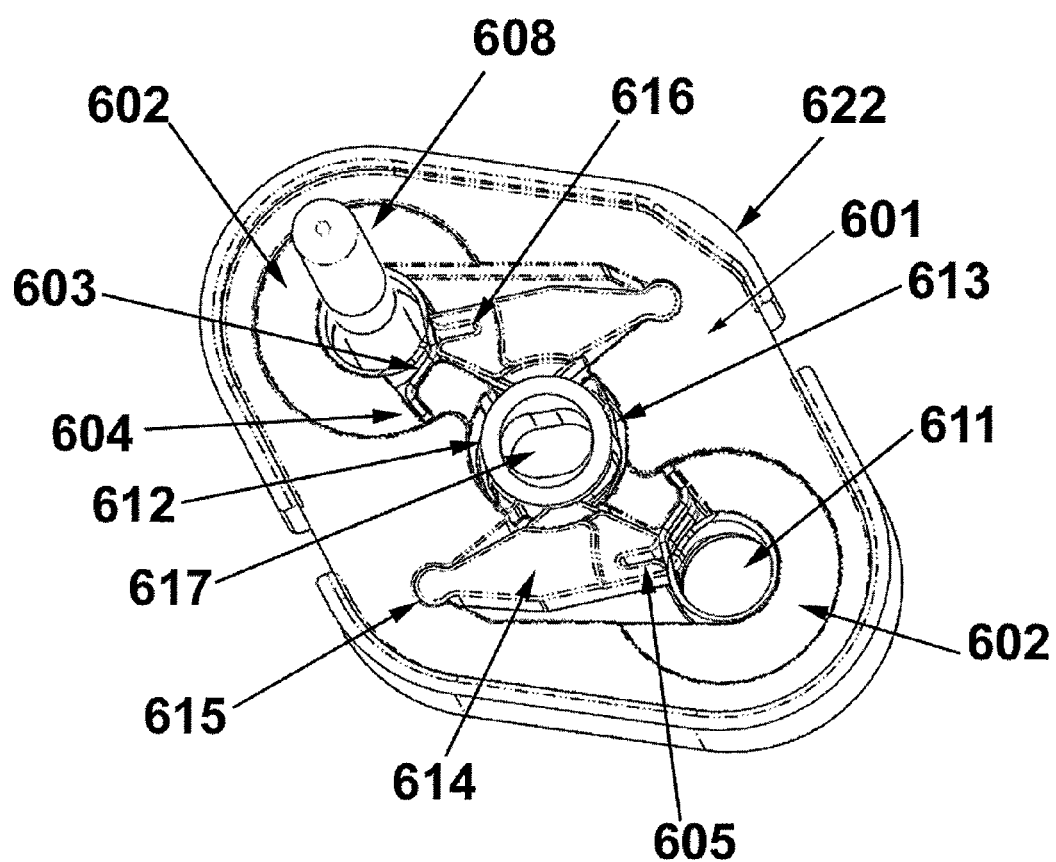
FIG. 27A is an isometric view of a two lumen active seal incorporating a controlling mechanism, according to certain embodiments.

FIG. 27A is an isometric view of a two lumen 611 active seal incorporating a controlling mechanism, according to certain embodiments. The seal is composed of a base or body 601, which includes two lead port seal tubes 602 with pin receiving portions formed of lumens 611 to accept passage of a lead 608. A separate moving element of the structure is a rotating cam 612. As the cam 612 is rotated, the ramp 613 on the surface of the cam 612 contacts and moves a slider 614. Further rotation of the cam 612 will then force the slider 614 to rotate around its fixed anchor point 615 in the plastic block (not shown). The opposite end of the slider 614 contains a slot 616, which entraps the moveable tab 605 of the seal's cinch 603 (See FIG. 25). Moving the moveable tab 605 of the cinch 603 engages or activates the seal by compressing seal tube 602 outer diameter to a smaller dimension. In this state, the lead's conductive surfaces are isolated and the lead 608 is held in place by the increased frictional forces. The activated seal also fluidly isolates adjacent electrical connection contacts from each other. As a result, the lead conductive surface with its associated electrical connection contact together are fluidly isolated from other adjacent electrical connections and stackable blocks.

According to FIG. 27A, the cam 612 comprises a shaped opening 617 at its center. This opening 617 accommodates the central shaft (See, e.g., FIG. 28) having a shape complementary to the opening 617 so that when rotated, the shaft forces the cam 612 to rotate. Once the mechanism rotates the cam 612 to its fully engaged position, it will remain in that position. Reverse rotation of the cam 612 will relax the forces on the slider 614, allowing the spring forces from the metallic cinch 603, to expand the cinch 603 and release the seal. In this relaxed state, the lead 608 can move freely.

Figure 27B:
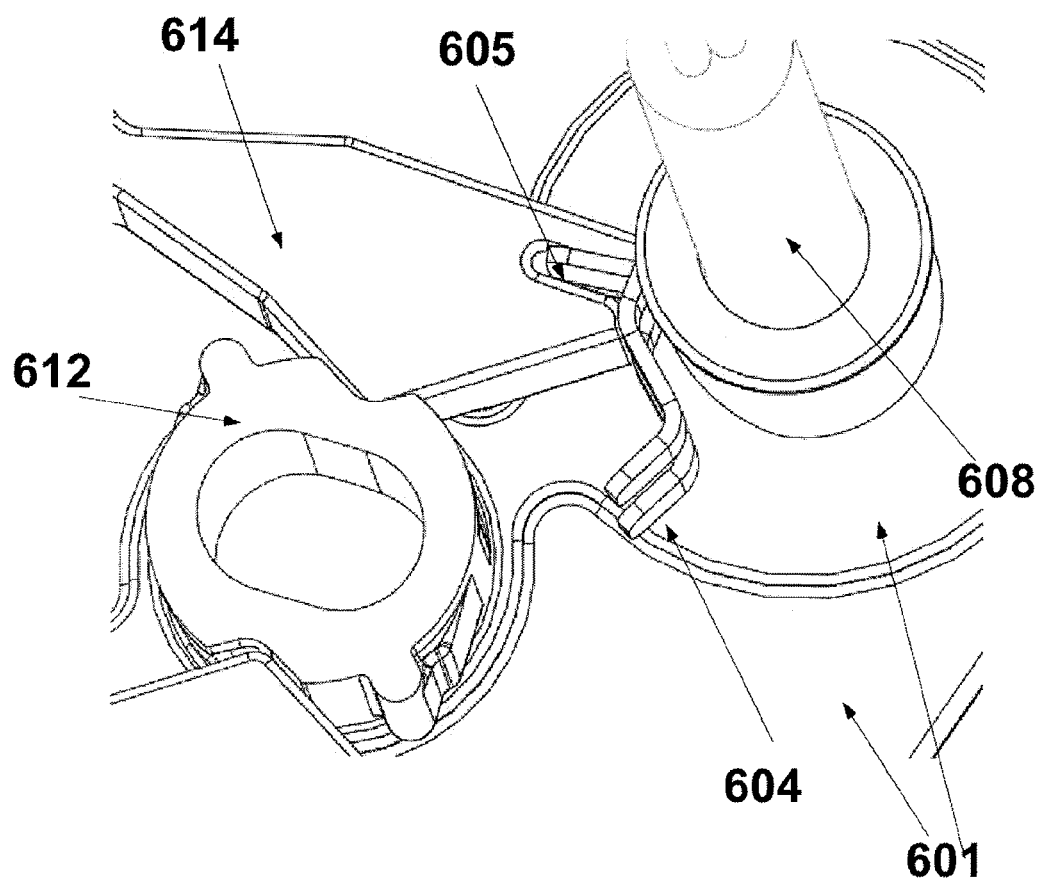
FIG. 27B is a magnified view of the active seal mechanism, according to certain embodiments.

FIG. 27B is a magnified view of the active seal mechanism. The lead 608 can be seen inserted into one of the lumens 611 of the seal 601. The cam 612, in this instance, is not yet pressing against the slider 614. However, the slider 614, still grasps the moveable tab 605 of the cinch. The fixed position tabs 604 of the cinch are visible in their retained position.

Figure 27C:
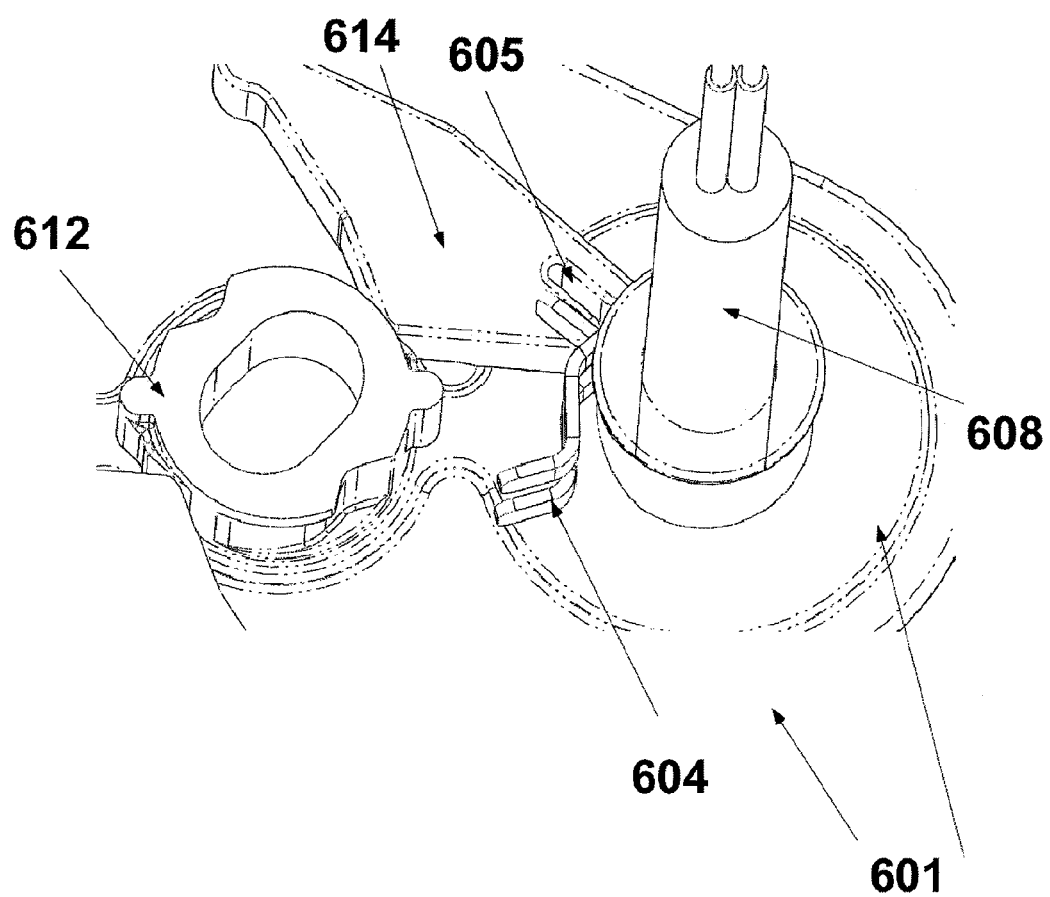
FIG. 27C is a magnified view of the active seal mechanism with the cam rotated to the latched position.

FIG. 27C is a magnified view of the active seal mechanism with the cam 612 rotated to the latched position. Slider 614 is moved maximally to force the moveable tab 605 so that the cinch has its smallest diameter and tightly grasps the lead body 608. Fixed position tab 604 remains fixed to its position, retained in place by in the block (not shown).

According to certain embodiments, the cam 612 and/or the slider 614 may also be associated with a portion of an electrical connection contact such as tab 342, 362. In this embodiment, a stackable block, e.g., block 220, may include both the seal 600 as well as the electrical connection contacts 340, 360. Rotation of a shaft associated with cam 612 and/or slider 614 may result in engagement of the seals and the electrical connection contacts. That is, the same controlling mechanism may be responsible for engaging both the seals and the electrical contacts. Accordingly, rotating cam 612 may rotate slider 614 causing each of the movable tab 605 and one or more of tabs 342, 362 provided on electrical connection contacts 340 and 360 to rotate into an activated position. In other embodiments, separate rotatable cams are associated with each of the electrical contacts and the seals, and each cam is responsible for causing its corresponding seal or electrical connection to move between the active and relaxed positions. For example, one stackable block 220 may be associated with an electrical connection contact 340, 360 and a cam 330 for controlling the diameter of the contact, while another stackable block 622 may be associated with a seal 600 and a cam 612, and the stackable blocks 220, 622 may be operably coupled to one another. As a result, in an active seal state, the seal 600 fluidly isolates the electrical connection contact in the adjacent stackable block 220 from the stackable block 622 having the seal 600.

Figure 28:
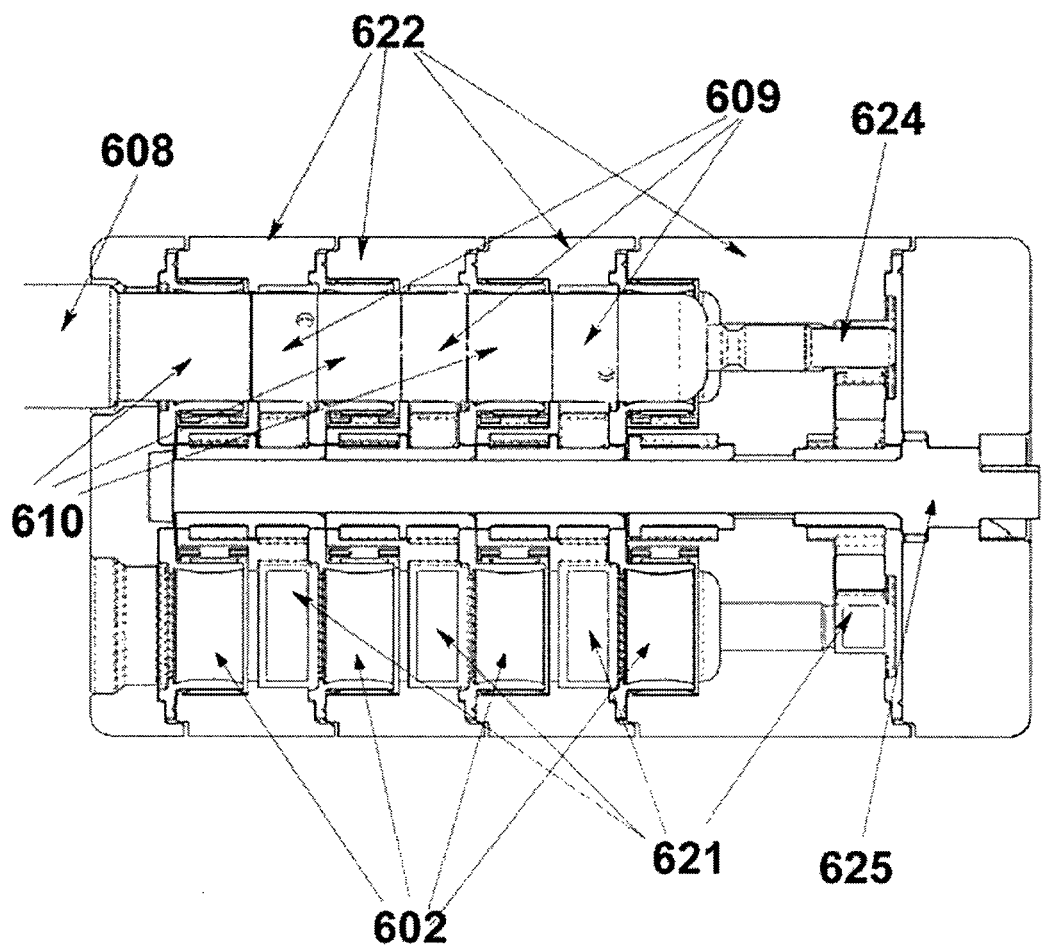
FIG. 28 is a cross-sectional view of a connector block assembly for an implantable device, according to certain embodiments.

FIG. 28 is a cross-sectional view of a connector block assembly for an implantable device, according to certain embodiments. The examples of leads 608 show conductors as three rings 609 and an end pin 624 on each lead 608. The lead 608 is shown inserted into the connector assembly which is comprised of a plurality of blocks 622, which sandwich active seals, e.g., including seal tubes 602, between the blocks. Along the body of the lead 608, the seals partition the electrical contacts 621, which connect to the lead's conductors 609, 624 into separate isolated sections. The centrally located activating shaft 625, which powers the cam of FIG. 27A, runs the full length of the assembly.

Figure 29:
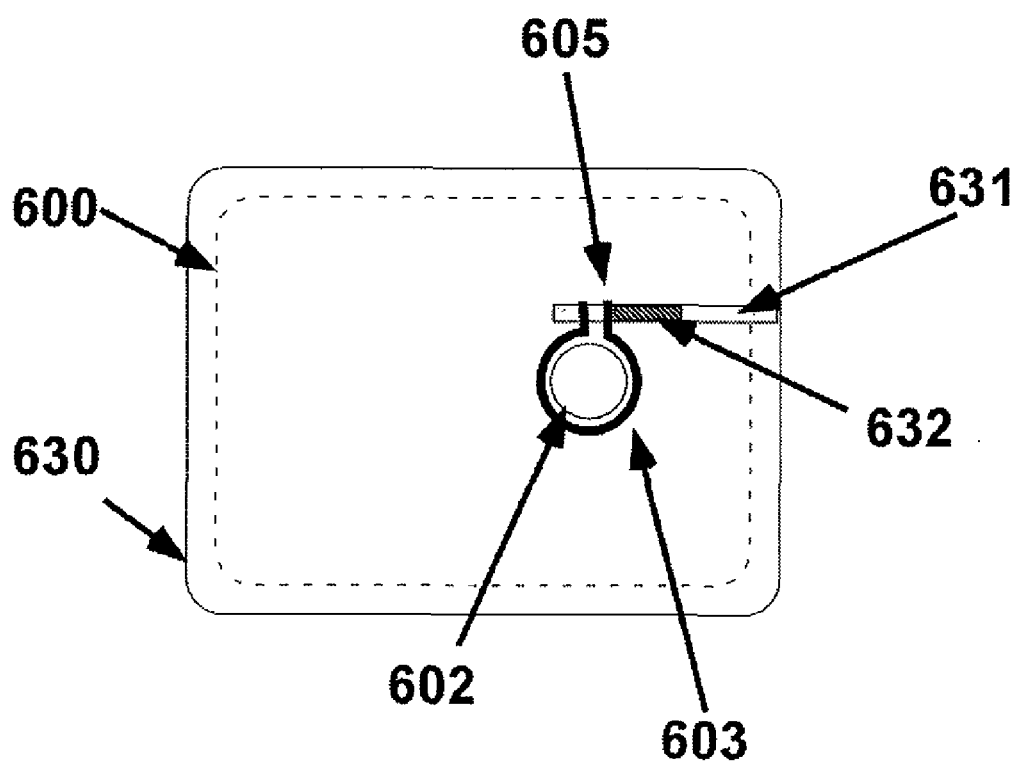
FIG. 29 is a schematic view of an alternative method of operating the seal.

FIG. 29 is a schematic of a cross section of a connector block 630 showing an alternative driving mechanism. The connector block 630 incorporates a seal 600 in one or more places. The cinch 603 with its attached moveable tab 605 surrounds the seal tube 602 as in previous figures. The connector block 630 body is penetrated by a threaded screw hole 631 that allows a screw 632 to travel from the outer edge of the connector 630 and impinge on the moveable tab 605. Further travel of the screw 632 will then force the tab 605 to move. The moveable tab 605 movement will reduce the diameter of the cinch 603 and compress the seal tube 602 in a manner similar to that depicted in FIGS. 27A and 27B. The screw serves as an alternative forcing structure to actuate the seal. Release of the seal tube's 602 compression is accomplished by reversing and removing the screw 632.

Additionally, according to certain embodiments, the active forces of the seal may isolate intentional fluids introduced in the body of the connector. Intentional fluids may include dielectric fluids such as mineral oil or mixtures containing mineral oil and may be included in, for example, pin receiving portions in order to provide lubricating properties, which may reduce the friction between the pin and inner surface of the seal tube and/or the electrical connection contact, thus reducing insertion forces. The intentional fluid may also serve as a hydrophobic fluid to oppose the intrusion of body fluids and other fluids, as an insulator by incorporating an intentional fluid with an appropriate dielectric coefficient, and/or as an isolator for isolating one contact from another. The intentional fluid may be a cleaning agent for dissolving organic debris such as blood. An antimicrobial chemical may be emulsified or dissolved into the fluid to prevent the growth of infectious entities such as bacteria or viruses on internal surfaces of the electrical connection apparatus or on the outer surface of the pin.

According to certain embodiments, the optimal, aligned and/or correct position of the lead once properly received in connector block is confirmed by way of a visual indicator. For example, the visual indicator may become visible or be activated once the lead is fully inserted in the connector block, which may correspond to the electrically conductive portions of lead 608 aligning with the electrical connection contacts of the connector block. In addition or alternatively, the visual indicator may become visible or be activated once the connecting block has correctly latched the lead into place by a cam mechanism as described in the various embodiments of FIGS. 14-29. The visual indicator may also become visible or change state in response operations associated with the connector block, as will become apparent in view of the following disclosure.

Figure 30A:
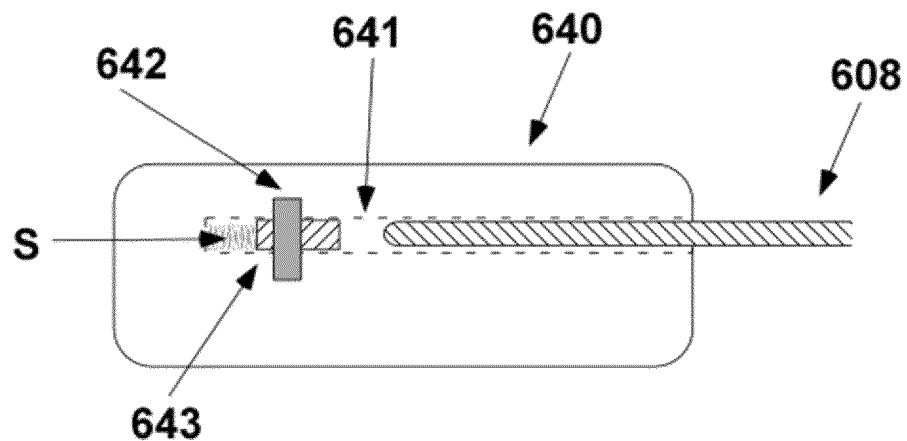
FIG. 30A depicts a mechanical indicator in a connector block in which a fiducial is hidden.

FIG. 30A depicts a cross-sectional view of a connector block having a visual indicator incorporated therein. According to FIG. 30A, a connector block 640 including a receptacle 641 or pin receiving portion, electrical connection contacts, and a visualization element 643, has not yet received the lead 608 or pin within the receptacle 641 to a fully inserted or a full and optimal position. As a result, the visualization element 643 provided as an insertion indicator arranged at a proximal part of the receptacle 641, is not yet visible. The visualization element 643 has on its outer surface a fiducial mark "M," in this example a black band (See FIG. 30B). An opaque component 642 at the proximal end of the receptacle 641 conceals the fiducial mark M, thus indicating the lead 608 or pin is not fully inserted.

Figure 30B:
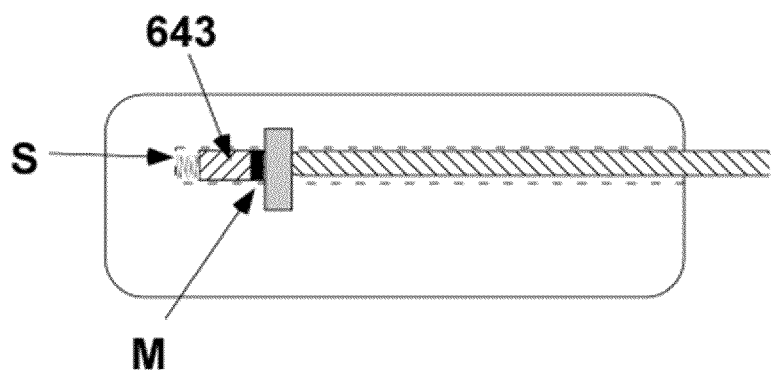
FIG. 30B depicts the mechanical indicator of FIG. 30A when lead is inserted in the connector block and fiducial is visible.

FIG. 30B depicts a cross-sectional view of the connector block 640, as in FIG. 30A, in which the lead 608 has been fully inserted into the receptacle 641. It has impinged upon and moved the visualization element 643. Thus the fiducial mark M on the visualization element 643 is exposed, and indicates to the user that the lead 608 is optimally placed. In some embodiments, and as shown in FIGS. 30A and 30B, the visualization element 643 may be coupled to a mechanical energy storage component, such as a spring "S," to return the visualization element 643 to no longer show the fiducial mark M, in the case where the lead was subsequently withdrawn or misaligned during the implant procedure.

Figure 30C:
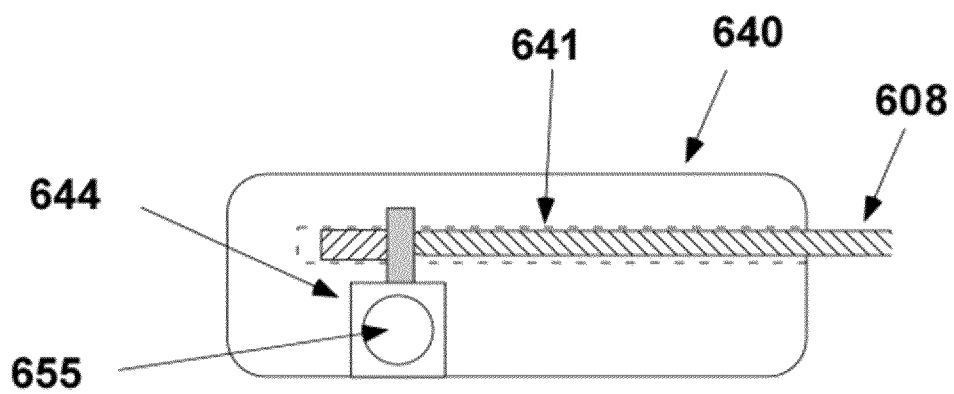
FIG. 30C depicts a cross-sectional view of another connector block in which an electrical insertion indicator including an indicator light is provided.

FIG. 30C depicts a cross-sectional view of another connector block 640 in which an electrical insertion indicator 644 including an indicator light 655 is provided. According to the embodiment of FIG. 30C, a pin is inserted into the receptacle 641 and the state of the insertion indicator light 655 changes from a first state to a second state and indicates to the user that the lead 608 or pin has been correctly inserted. The insertion indicator light 655 may also change state when the lead 608 has been improperly inserted and/or upon removal of the lead. The insertion indicator 644 may include conductive elements coupled to the indicator light to deliver power for changing the state of the indicator light 655. Optionally, the insertion indicator 644 may include a power source coupled to the conductive elements for providing power to the indicator light 655.

According to certain embodiments, the indictor light 655 receives power from a power source external to the connector block. The power source may be removably associated with a conductive portion of the connector block, and upon correct insertion of the lead 608, for example, the coupled power source delivers power to the indicator light 655 via electrical conductors of the conductive portion. For example, the connector block may include switches (See FIG. 35) that move in response to insertion of the lead 608, which results in a completion of an electrical circuit so that the indicator light 655 changes state. According to certain embodiments, the indicator light 655 may also change state upon coupling with the power source and/or upon latching the lead 608 within the pin receiving portion.

Figure 31A:
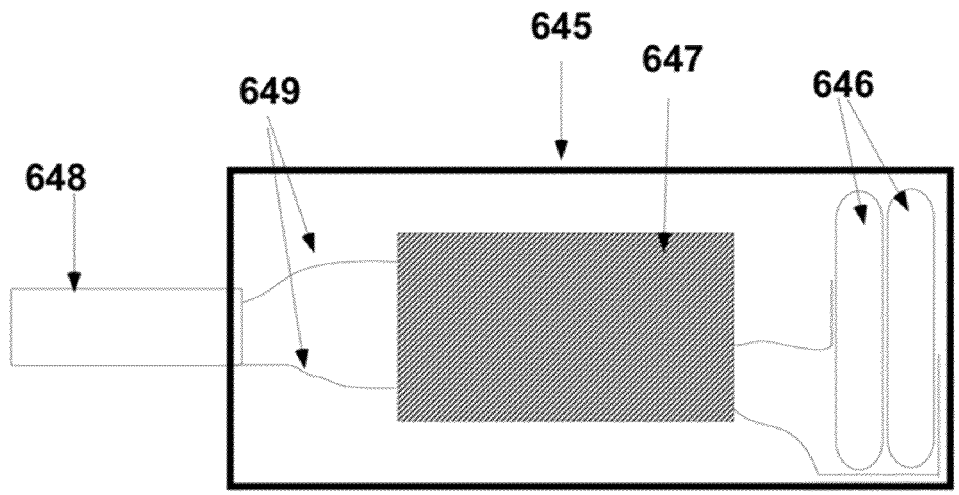
FIG. 31A depicts cross-section of a latching tool for latching leads to a connector block including power for indicators.

FIG. 31A depicts a tool including a power source 646 for removably coupling to a connector block having an associated insertion indicator light 655. The tool may also serve as a latching mechanism for a connector block, such as the connector blocks depicted in FIGS. 14-29 and FIG. 31B, which include an activating shaft. The tool thus includes a body 645 of a generally round cylindrical shape, with an engaging shaft portion 648 extending beyond one end of the body 645 that may rotate to reduce a diameter of an electrical connection contact around the lead 608. Inside the body 645 of the tool, in addition to the power source 646 such as batteries, are additional electrical circuitry 647 and conductors 649 such as wires to connect to the engaging shaft portion 648.

Figure 31B:
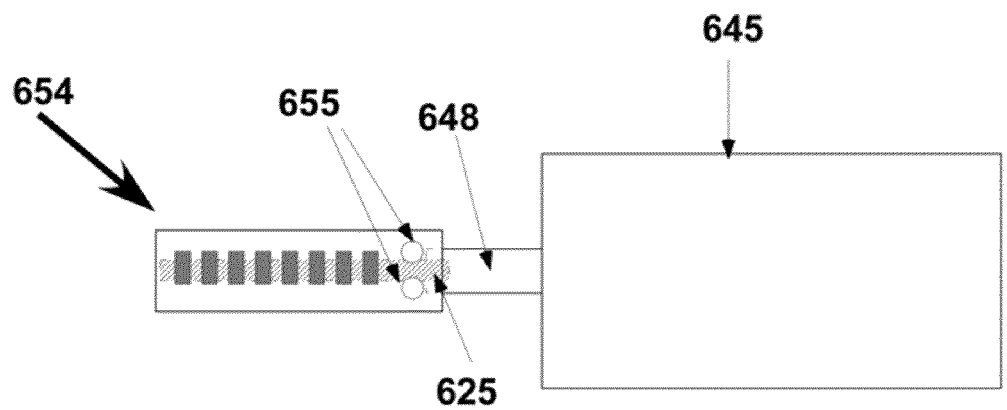
FIG. 31B depicts the latching tool in relative position when engaged with a connector block.

FIG. 31B depicts the engaging shaft 648 of the powered tool engaging the activating shaft 625 of connector block 654. The connector block 654 includes components described above in connection with FIGS. 1-29, and additionally includes an insertion indicator including indicator lights 655 on an outer surface of the connector block 654. When the engaging shaft 648 is connected to the connector block 654, one or more of the indicator lights 655 may change state to indicate the power source within the tool is electrically coupled to the connector block. With the power source coupled to the connector block 654, insertion of a lead 608 (See FIG. 30C) in a pin receiving portion results in one or more indicator lights 655 changing state, for example, to indicate correct lead insertion or incorrect lead insertion. According to some embodiments, rotation of the engaging shaft 648 results in latching of the activating shaft 625, which reduces a diameter of the electrical connection contact around the lead 608 causes one or more indicator lights 655 to change state. After confirming the correctness of the various connecting and mechanical operations, the tool is removed from the connector block 654 in a manner that does not affect the insertion state of the lead 608 and/or the latching status of the activating shaft 625.

Figure 32:
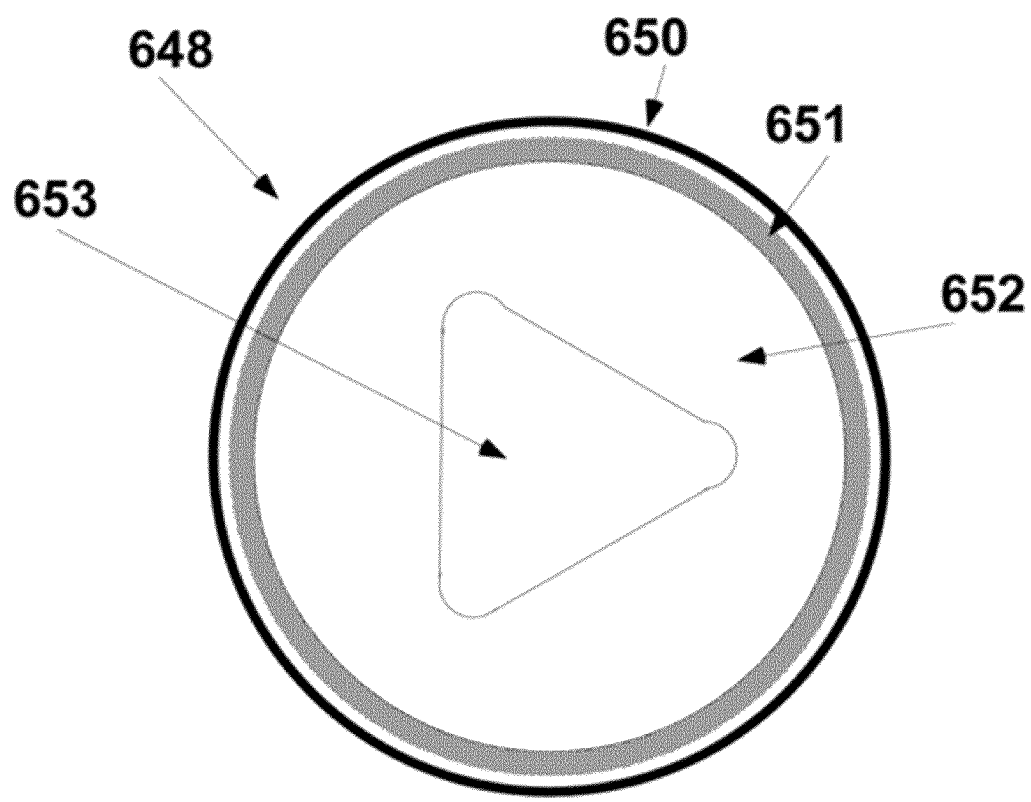
FIG. 32 is an end view of the engaging shaft of the engaging tool.

FIG. 32 is an end view of the engaging shaft 648. The engaging shaft 648 comprises a series of co-axial elements. An outer element is a conductive cylindrical shaft 650, for example, provided as the outer surface of the engaging shaft 648. The middle element is provided as a main solid shaft 652 and includes a socket shape 653 configured to engage with a latching or activating shaft of the connector block (See e.g., FIG. 31B) and to withstand torque as the engaging shaft 648 rotates to latch the connector block. Between the cylindrical shaft 650 and the inner shaft 652 is an insulating cylinder 651, which electrically isolates the inner shaft 652 from the outer shaft 650. This co-axial construction of rigid components and electrically conductive components allows the simultaneous application of mechanical torque to operate the latching shaft of the connector block, and the application of electric power to operate the visual indicators in the connector block.

Figure 33:
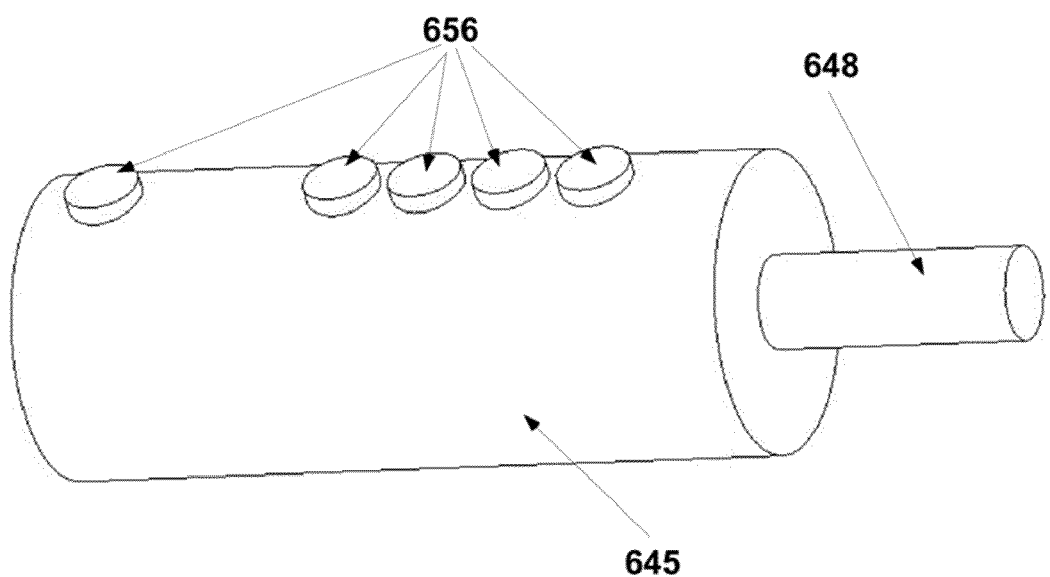
FIG. 33 is an isometric view of an indicating tool with indicators on the tool itself.

FIG. 33 depicts an isometric view of an indicating tool including insertion indicators 656 on the body 645 of the tool. The engaging tool delivers latching mechanism operation torque as well as electrical power to the connector block via the engaging shaft 648. Circuitry provided within the tool discriminates, by means of the connector block internal switches and resistors, which indicators 656 should illuminate. It will be understood that because the indicating tool includes insertion indicators 656, a connector block may not necessarily include indicator lights, but rather may include components such as switches and/or resistors that enable the indicators 656 to change state upon engagement with the connector block and/or upon sensing the lead 608 has been inserted in the connector block. Because the tool cooperates with the connector block for a variety of purposes, the indicators 656 may change state to provide a user with an indication of a variety of operational statuses. For example, the connector block may include an activating shaft switch that cooperates with an activating shaft indicator light to indicate the activating shaft has been moved to a latched or an un-latched state. An indicator light and associated switch may also be provided for indicating the tool is connected to the connector block. Of course, the indicating tool and connector block may each be provided with indicators 655, 656 to provide indications of operational status.

Accordingly, as will be appreciated, the above-described insertion indicators 655, 656 arranged on the connector block 654 and tool, respectively, may be provided as single state or multi-state indicators, and may be arranged on one or both of the connector block and the engaging tool. For example, illuminators on an exterior surface of the engaging tool may be a pair of single state indicators, one multi-state indicator, a number of multi-state indicators, or a combination of single and multi-state indicators. An illuminator may be associated with a single pin receiving portion of the connector block, e.g., an illuminator may be provided for each pin receiving portion. Alternatively, one illuminator may be associated with all pin receiving portions. In addition, the illuminator may be capable of different presentations for one or the other state of the leads, the tool-connector block connecting status, and/or the latching status of the connector block. For example, a first state (e.g., an illuminated state) of the indicator light may correspond to coupling of the connector block and tool and/or to correct insertion of the pin in the pin receiving portion and/or to a latched status of the cam shaft. A second state (e.g., non-illuminated state) may correspond to an incorrect coupling of the connector block and tool and/or to incorrect insertion or non-insertion of the pin and/or to a non-latched status of the cam shaft. Alternatively, the indicator light may indicate a coupling, insertion and/or latching state by blinking, by remaining illuminated for a predefined period of time, or by changing between any of a constantly illuminated state, an off state or a blinking state. In another example, a light of a specified color (e.g., green) may provide a first indictor state, and a light of another specified color (e.g., red) may provide a second indicator state. A single indicator light may be illuminated in multiple colors, with one color illuminated to indicate a first state of the insertion indicator light and another color different from the first may illuminate to indicate a second state of the insertion indicator light. Of course, each indicator may be changed between more than two states in order to signal the status of insertion and/or connection.

Figures 34A, 34B:
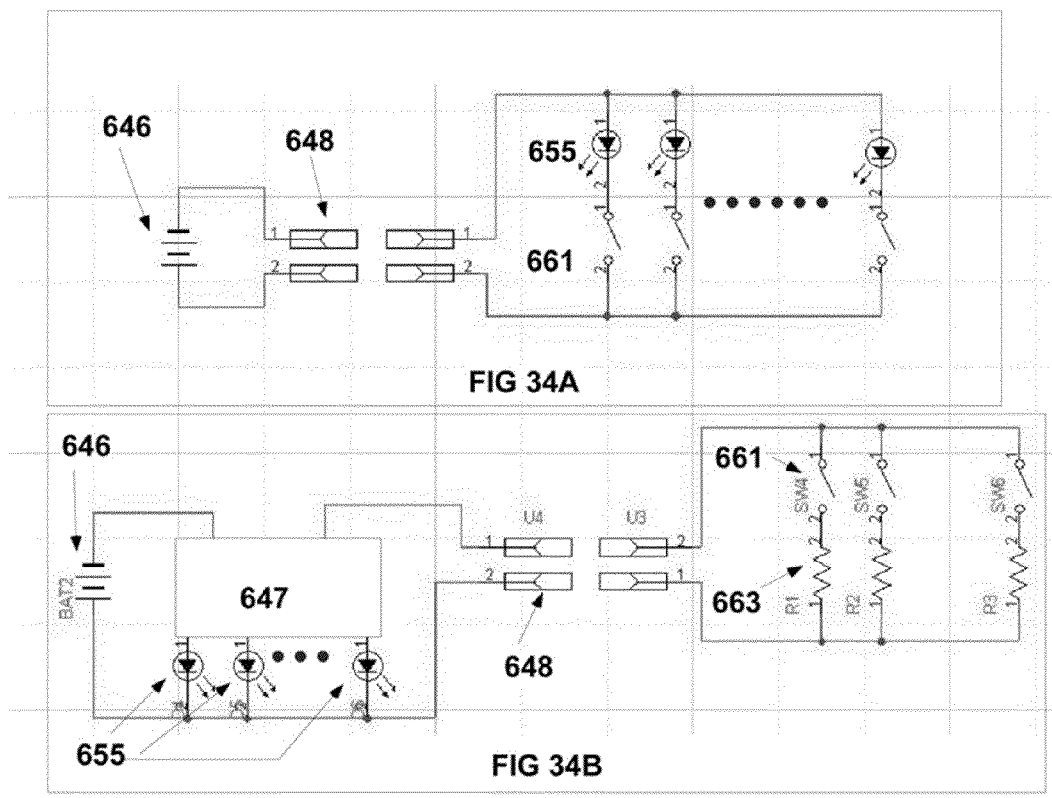
FIG. 34A is an electrical schematic of one implementation of LED indicators in the header.
FIG. 34B is an electrical schematic of one implementation of indicators and electronics in the latching tool.

FIG. 34A depicts an electrical schematic in which the indicators 655 and the associated switches 661 are provided in the body of the connector block. Power is supplied by battery 646 inside the latching tool. The electrical power passes through the co-axial shaft's conductors 648 and into the switches 661 and indicators 655 in the connector block. There may be one or multiple pairs of indicators and switches. For example, an indicator switch 661 and indicator light pair 655 may be associated with one pin receiving portion. The switch 661 may be moved, for example from an opened to a closed position or vice versa, upon proper positioning of the implantable lead and the associated indicator 655 indicates the proper positioning by changing state, e.g., by changing from an illuminating, blinking, off or color state to a different state. According to certain embodiments, the switches 661 are momentary switches and may include a lever portion, which moves upon correct insertion to the lead 608. In other embodiments, permanent switches may be provided.

FIG. 34B depicts an electrical schematic in which indicators and associated electronics are provided in the latching tool. Power is supplied by battery 646, which drives the electronics 647. Sensing electrical current is passed through the tool's co-axial shaft's conductors 648 and through some of the switches 661 and companion unique resistances 663. The resulting unique current flow, is discriminated by the electronics 647 which then applies power to the appropriate indicators 655 located on the handle of the tool itself.

Figure 35:
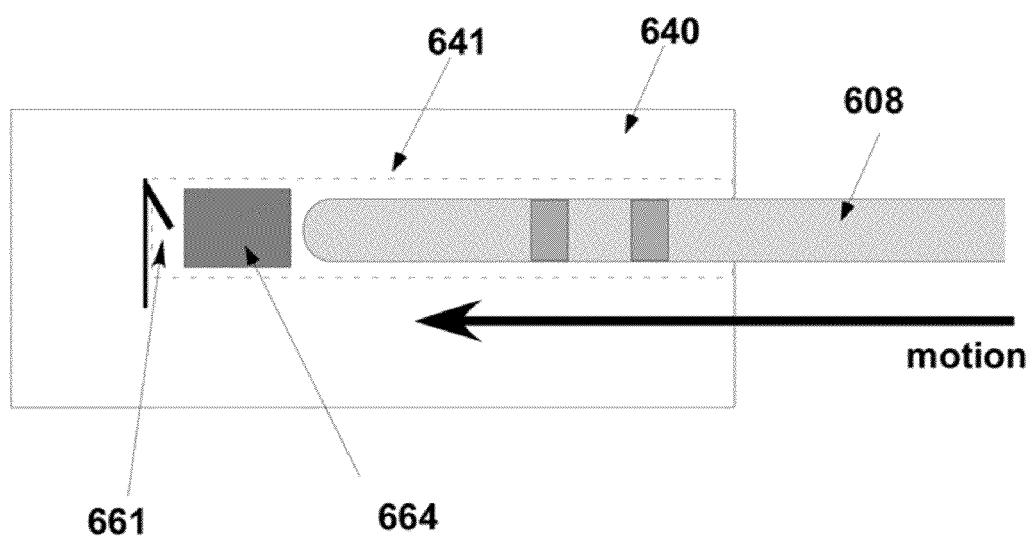
FIG. 35 depicts a cross-section of a connector block in which a rod assists closing an indicator switch.

FIG. 35 depicts a cross-section of a connector block in which a rod 664 assists actuating an indicator switch 661. As the lead 608 is inserted into the connector block housing 640 through the lead receiving receptacle 641 or pin receiving portion, the rod 664 is contacted by the lead 608 and is moved to actuate indicator switch 661. Thus, in FIG. 35, the receptacle 641 is additionally provided with the rod 664 proximate the switch 661 and facilitates switch actuation. The rod 664 may be provided as an insulating plug, and where the lead is electrically conductive at its terminal end, for example, the rod 664 electrically isolates the lead 668 from the electrically conductive components of the insertion indicator. In another example, the lead may be shorter than the length of the lead receiving receptacle 661, and the rod 664 may be provided to ensure actuating of the switch 661 upon correct insertion of the lead. Accordingly, when the lead 608 is in its correct position in the receptacle 661, the rod 664 actuates or presses the lever to move the switch 661 to an open or closed position, and the lead insertion indicator provides the user with an indication the lead has been correctly inserted. Of course, indicator switches may be provided on the connector block in areas where the engaging shaft couples to the connector block and/or where the engaging shaft engages a cam shaft.

Figure 36:
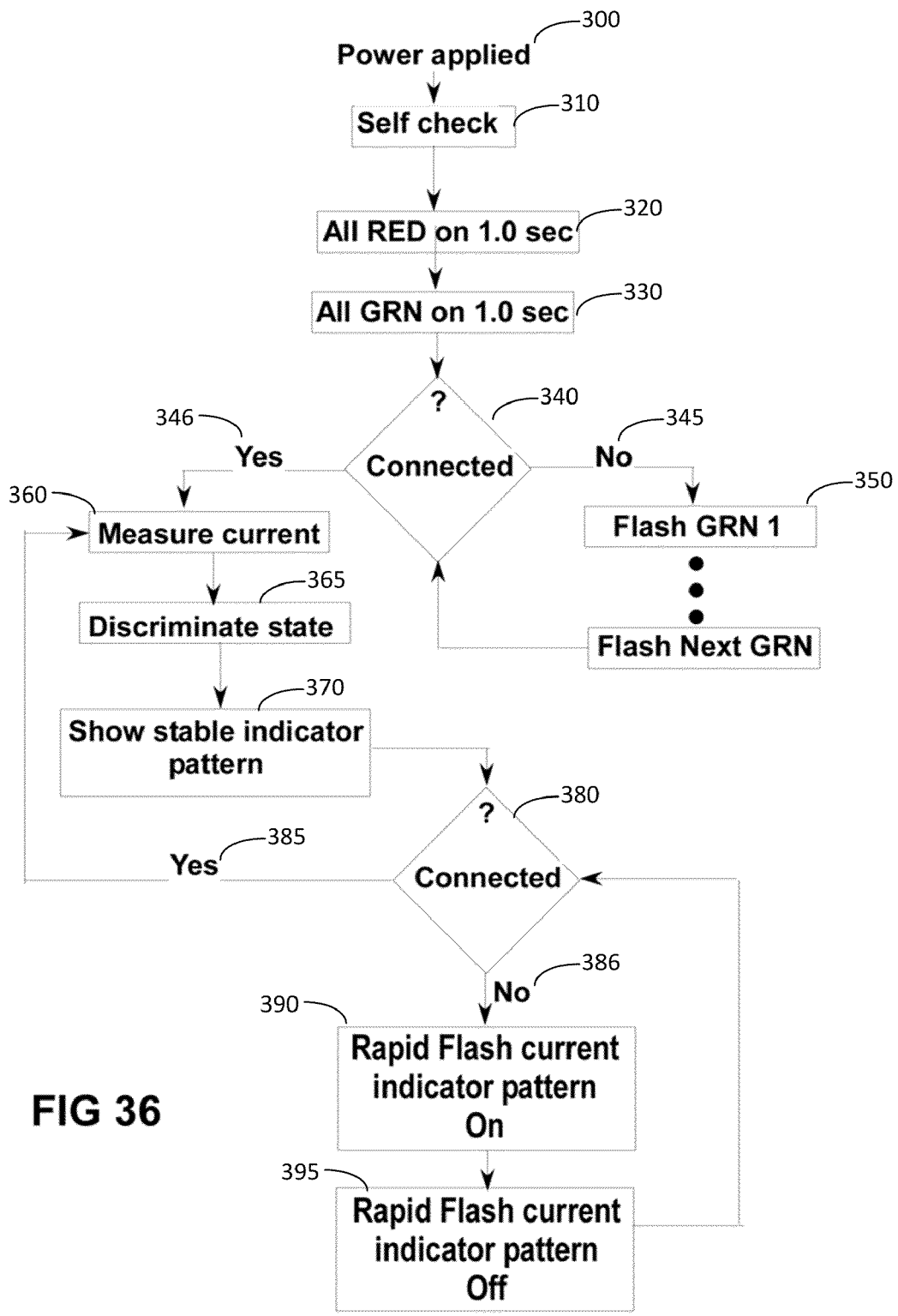
FIG. 36 is a flowchart of a method for indicating a lead has been correctly inserted in the connector block.

FIG. 36 is a flowchart of a method for indicating a lead has been correctly inserted in the connector block. That is, according to certain embodiments, computer-implemented software or firmware residing in the electrical connection apparatus, the engaging tool or on a device communicatively coupled to the electrical connection apparatus and/or the engaging tool, provide signals to the indicators 655, 656 to control the lighting state. The software or firmware is communicatively coupled to a processor and memory, and controls the operating state of the indicators. The lighting states that may be controlled by the software may include, for example, an on/off state, duration of on/off state, light color state, and/or pulse rate. For example, when the indicators 655 and/or 656 are provided as LEDs, the lighting state may change from on to off, from off to on for a predefined duration, from red to green to blue or another color, and/or may change a time interval at which the LED pulses from on to off.

According to certain embodiments, operation of software or firmware initially involves establishing a circuit connection to a power source (operation 300), such as a battery provided within the engaging tool. For example, a switch or the removal of an insulation tab that blocks the electrical current flow may establish the connection. A self check is performed (operation 310) to confirm valid firmware/software content and general operational status of the associated device. An indicator test may then be performed by illuminating some or all of the indicators. For example, each indicator for signaling incorrect or non-insertion of the lead, e.g., red LEDs, may be illuminated for one second (operation 320), and then each indicator for signaling correct insertion of the lead, e.g., green LEDs (operation 330), may be illuminated for one second, which allows the operator to visually confirm that all the indicators are operational. Then the indicators would be turned off.

A check of whether the engaging tool is connected with the connector block (operation 340) resulting in a negative connection (operation 345) results in commencing a sequence of indicator flashing the indicators (operation 350), e.g., the green indicators would commence flashing. Each indicator may be flash for a fraction of a second, followed by an adjacent indicator flashing. For example, the sequence of flashing green lights shows the tool is powered, the firmware is operating, and the tool is not yet in communication with the connector block, and therefore the status of the latching and the leads is unknown.

When the check shows a positive connection between the engaging and the connector block (operation 346), current flows from the tool through the connector block, and the resistance value presented to the current flow is analyzed (operation 360). Each state of the connector block is uniquely represented by a resistance value (operation 365). Thus for four (4) leads and a latching indicator there would be 32 states. The software/firmware then determines which indicators should be red and which should be green. The flashing is halted and a presentation of the status of each lead and the latching status is portrayed (operation 370).

While the tool is in communication with the connector block, the status of the connector block is re-evaluated (operation 380), for example, every 100 milliseconds, and if still connected (operation 385), the indicator portrays and tracks any changing status (operations 360-370). When the tool is removed from the connector block the connection check (operation 380) results in a negative indication (operation 386), the last known status remains portrayed on the tool's indicators, but each indicator blinks (operations 390 and 395), e.g., at a 5 Hz rate, to show the status is not current.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

Although the present invention has been described with reference to preferred embodiments, persons skilled in the art will recognize that changes may be made in form and detail without departing from the spirit and scope of the invention.

What is claimed is:

1. An electrical connection apparatus comprising:
 a connector block comprising at least one pin receiving portion defined by an inner wall within the connector block, the at least one pin receiving portion for receiving a pin of one of an implantable lead and an implantable medical device;

at least one electrical connection contact comprising a first portion disposed within the at least one pin receiving portion, the first portion for receiving the pin, and a second portion disposed at an exterior to the connector block, the second portion for coupling with the other of the implantable medical device and the implantable medical device, wherein the first portion and the second portion integrally form the at least one electrical connection contact; and an insertion indicator comprising an indicator light operably coupled to an indicator switch associated with the at least one pin receiving portion, wherein the indicator light is in a first state prior to the pin being received in the connector block and when the pin is incorrectly received in the connector block, and wherein the indicator switch actuates when the pin has been correctly received in the pin receiving portion and causes the indicator light to assume a second state different from the first state.

2. The electrical connection apparatus of claim 1, wherein one of the first or the second state corresponds to an illuminated state of the indicator light, and the other state corresponds to a non-illuminated state of the indicator light.

3. The electrical connection apparatus of claim 1, wherein one of the first or the second state corresponds to a first light color, and the other state corresponds to a second light color different from the first color.

4. The electrical connection apparatus of claim 1, wherein a force exerted on the switch by advancing the pin in the pin receiving portion causes the indicator light to change state.

5. An electrical connection apparatus and a power source for removably coupling with the electrical connection apparatus, wherein the electrical connection apparatus comprises:
a connector block comprising at least one pin receiving portion defined by an inner wall within the connector block;
at least one electrical connection contact comprising a first portion disposed within the at least one pin receiving portion, the first portion for receiving a pin, and a second portion disposed at an exterior to the connector block, wherein the first portion and the second portion integrally form the at least one electrical connection contact; and
an insertion indicator comprising an indicator light operably coupled to an indicator switch, the indicator switch associated with the at least one pin receiving portion and comprises electrical conductors at the exterior of the connector block; and
wherein the power source is removably associated with the connector block;
wherein upon connecting the power source with the electrical conductors and incorrect insertion of the pin in the pin receiving portion, the indicator light assumes a first state, and upon connecting the power source with the electrical conductors and correct insertion of the pin in the pin receiving portion, the switch and couples the electrical conductors such that the connected power source delivers power to the indicator light to cause the indicator light to assume a second state different from the first state; and
wherein upon removing the power source, the pin remains in the correct position.

6. The electrical connection apparatus of claim 5, further comprising an engaging tool for engaging the electrical connection apparatus, wherein the engaging tool houses the power source and is removably associated with a portion of the exterior of the connector block comprising the electrical conductors.

7. The electrical connection apparatus of claim 6, further comprising an activating shaft that runs longitudinally in the connector block, wherein the engaging tool engages with the activating shaft and rotates the activating shaft such that the activating shaft moves the first portion to reduce a diameter of the first portion around the pin.

8. The electrical connection apparatus of claim 6, wherein the engaging tool comprises a conductive cylinder that contacts the electrical conductors and delivers power from the power source to the electrical conductors.

9. An electrical connection apparatus and an engaging tool for removably coupling with the electrical connection apparatus, wherein the electrical connection apparatus comprises:
a connector block comprising at least one pin receiving portion defined by an inner wall within the connector block;
at least one electrical connection contact comprising a first portion disposed within the at least one pin receiving portion, the first portion for receiving a pin, and a second portion disposed at an exterior of the connector block, wherein the first portion and the second portion integrally form the at least one electrical connection contact; and
an indicator switch operably coupled to the pin receiving portion, wherein the indicator switch comprises electrical conductors extending to the exterior of the connector block; and
wherein the engaging tool comprises:
a power source;
an insertion indicator comprising an indicator light coupled to the power source; and
an engaging shaft for removably engaging with the connector block, wherein the engaging shaft is coupled to the power source and comprises an electrically conductive area for coupling to the electrical conductors of the indicator switch;
wherein when the engaging tool is engaged with the electrical conductors at the exterior of the connector block and the pin has been correctly received in the pin receiving portion, the indicator switch couples the electrical conductors with the power source so that the indicator light is in a first state; and
wherein the indicator light is in a second state different from the first state when the engaging tool is engaged with the connector block but prior to the pin being received in the pin receiving portion.

10. The electrical connection apparatus and engaging tool of claim 9, wherein the indicator light first or second state corresponds to an illuminated state, and the other state of the indicator light corresponds to a non-illuminated state.

11. The electrical connection apparatus and engaging tool of claim 9, wherein the indicator light first or second state corresponds to a first light color, and the other state of the indicator light corresponds to a second light color different from the first color.

12. The electrical connection apparatus and engaging tool of claim 9, wherein the insertion indicator further comprises another indicator light that is in a first state prior to the pin being received in the connector block and the pin being incorrectly received in the connector block, and is in a second state upon correct insertion of the pin, wherein the first state and second state of the indicator light differ from the first state and the second state of the another indicator light.

13. The electrical connection apparatus and engaging tool of claim 12, wherein the another indicator light first or second state corresponds to an illuminated state, and the other state of the another indicator light corresponds to a non-illuminated state.

14. The electrical connection apparatus and engaging tool of claim 12, wherein the another indicator light first or second state corresponds to a first light color, and the other state of the another indicator light corresponds to a second light color different from the first color.

15. The electrical connection apparatus and engaging tool of claim 9, wherein the electrical connection apparatus comprises a plurality of indicator switches, each indicator switch operably coupled one pin receiving portion, wherein the indicator switches comprise electrical conductors extending to the exterior of the connector block and the insertion indicator of the engaging tool comprises a plurality of indicator lights, and wherein each indicator light is associated with one pin receiving portion.

16. The electrical connection apparatus and engaging tool of claim 15, wherein each indicator switch is associated with a resistance unique to the switch with respect to the plurality of indicator switches, and wherein the engaging tool comprises circuitry for identifying actuation of the particular switch and changes a state of a corresponding indicator light.

17. The electrical connection apparatus and engaging tool of claim 9, wherein the electrical connection apparatus further comprises an activating shaft that runs longitudinally in the connector block and an activating shaft switch operably coupled to the activating shaft and actuates in response to movement of the actuating shaft, wherein the activating shaft switch comprises electrical conductors for contacting the engaging tool extending to the exterior of the connector block, and the engaging tool further comprises an activating shaft indicator light, wherein when the engaging tool engages with the activating shaft and moves the activating shaft from an un-latched state to a latched state, the activating shaft switch is actuated to cause the activating shaft indicator light to change from a first state to a second state to indicate the activating shaft is in the latched state.

18. The electrical connection apparatus and engaging tool of claim 17, wherein the activating shaft indicator light first or second state corresponds to an illuminated state, and the other state of the activating shaft indicator light corresponds to a non-illuminated state.

19. The electrical connection apparatus and engaging tool of claim 17, wherein the activating shaft indicator light first or second state corresponds to a first light color of the indicator light, and the other state of the activating shaft indicator light corresponds to a second light color different from the first color.

20. The electrical connection apparatus and engaging tool of claim 17, wherein the engaging tool comprises a conductive cylinder for contacting the electrical conductors of the indicator light of the insertion indicator and the activating shaft indicator light, and upon contacting the electrical conductors, the conductive cylinder delivers power from the power source to the electrical conductors.

* * * * *

UNITED STATES PATENT AND TRADEMARK OFFICE
CERTIFICATE OF CORRECTION

| | | |
|---|---|---|
| PATENT NO. | : 8,206,175 B2 | Page 1 of 1 |
| APPLICATION NO. | : 12/857236 | |
| DATED | : June 26, 2012 | |
| INVENTOR(S) | : Garth W. Boyd et al. | |

It is certified that error appears in the above-identified patent and that said Letters Patent is hereby corrected as shown below:

CLAIMS

| Column | Line | PTO | Should Read |
|---|---|---|---|
| 23 | 55 | "the switch and couples the" | -- the switch couples the -- |

Signed and Sealed this
Second Day of October, 2012

David J. Kappos
*Director of the United States Patent and Trademark Office*